US006574629B1

(12) United States Patent
Cooke, Jr. et al.

(10) Patent No.: US 6,574,629 B1
(45) Date of Patent: Jun. 3, 2003

(54) PICTURE ARCHIVING AND COMMUNICATION SYSTEM

(75) Inventors: Robert E. Cooke, Jr., Mahwah, NJ (US); Michael G. Gaeta, Nanuet, NJ (US); Dean M. Kaufman, Maplewood, NJ (US); John G. Henrici, Florida, NY (US)

(73) Assignee: Agfa Corporation, Wilmington, MA (US)

( * ) Notice: Subject to any disclaimer, the term of this patent is extended or adjusted under 35 U.S.C. 154(b) by 0 days.

(21) Appl. No.: 09/221,282

(22) Filed: Dec. 23, 1998

(51) Int. Cl.[7] .............................................. G06F 17/30
(52) U.S. Cl. ...................................................... 707/10
(58) Field of Search ................................ 707/204, 205, 707/104.1, 10; 250/208.1; 340/310.02; 345/668, 733; 358/434; 382/128; 455/450, 451, 561; 600/300, 407, 425, 437; 709/228, 249; 710/107; 711/150, 166; 714/11, 48; 717/104

(56) References Cited

U.S. PATENT DOCUMENTS

| | | | | |
|---|---|---|---|---|
| 4,833,625 A | * | 5/1989 | Fisher et al. ................. | 364/518 |
| 4,847,694 A | | 7/1989 | Nishihara ..................... | 358/434 |
| 5,027,110 A | | 6/1991 | Chang et al. ................. | 340/731 |
| 5,140,518 A | | 8/1992 | Ema ........................ | 364/413.01 |
| 5,359,512 A | | 10/1994 | Nishihara .............. | 364/413.01 |
| 5,440,607 A | | 8/1995 | Nakaya ....................... | 378/98.2 |
| 5,469,353 A | | 11/1995 | Pinsky et al. .......... | 364/413.01 |
| 5,513,101 A | | 4/1996 | Pinsky et al. ................ | 364/401 |
| 5,655,084 A | * | 8/1997 | Pinsky et al. ................. | 707/619 |
| 5,668,998 A | | 9/1997 | Mason et al. ................ | 395/701 |
| 5,674,744 A | | 10/1997 | Tsujii ........................... | 395/203 |
| 5,734,915 A | | 3/1998 | Roewer ....................... | 395/773 |
| 5,740,267 A | | 4/1998 | Echerer et al. ............. | 382/132 |
| 5,835,735 A | * | 11/1998 | Mason et al. ............... | 395/287 |
| 5,949,491 A | * | 9/1999 | Callahan et al. ............ | 348/442 |
| 6,011,537 A | * | 1/2000 | Slotznick ..................... | 345/115 |
| 6,260,021 B1 | * | 7/2001 | Wong et al. .................... | 705/2 |

FOREIGN PATENT DOCUMENTS

EP        0380966        8/1990

OTHER PUBLICATIONS

DICOM: AN Introduction to the Standard By Steven C. Horiil et al—Sep. 1, 1998.

* cited by examiner

*Primary Examiner*—Diane D. Mizrahi
*Assistant Examiner*—Apu M Mofiz
(74) *Attorney, Agent, or Firm*—Paul A. Pysher; Brian L. Michaelis

(57) ABSTRACT

A picture archiving and communication system ("PACS") includes plural core components arranged in a cluster. These core components include an archive station which includes long-term storage for storing image data, and a reviewing station which includes a display for displaying images based on received image data. Also included is a network gateway which interfaces to a non-core component so as to receive image data therefrom, and which routes the image data to at least one of the archive station and the reviewing station based on a set of rules in the network gateway. Finally, a database server manages access to the image data, and stores information relating to the image data.

57 Claims, 26 Drawing Sheets

RS1 D
RS2 D
RS3 D
AS  D
NWG D
OS  D
RP5 D
IM1 T
IM2 T
IM3 T

FIG. 6

Routing Patterns

| Add Routing Pattern | Delete Routing Pattern | Modify Routing Pattern |
|---|---|---|

1. Click on Add Routing Pattern and enter the information:

99 — Add Routing Pattern

100 — Name for Routing Pattern  [Type the name here]

101 — Destination  [Select a station, e.g. RS1]

102 — Specialty  [Select a specialty or "Don't Care"]

103 — Study Status  [Select a status upon which routing occurs]

104 — Referring Physician  [Select a physician or Don't Care"]

105 — Apply Routing To  [Select "All" or Non-Prefetched only"]

106 — Off Peak Routing  [Select OFF or ON]

If Off PeakRouting is ON then select a Schedule Name:

107 — Off Peak Schedule Name  [Select weekdays, weekends, or weeknights]

2. Add the route by clicking Add Routing Pattern

3. To add more stations to this route, click Modify Routing Pattern and make the appropriate selections for that station

FIG. 8

Routing Patterns

[ Add Routing Pattern ] [ Delete Routing Pattern ] [ Modify Routing Pattern ]

Rules for Routing Pattern *MR/CT*

| Destination | Criteria | | | | |
| --- | --- | --- | --- | --- | --- |
| | Specialty | Study Status | Referring Physician | Patient Location | Arrival Time |
| RS7 | BODY | New | Don't Care | Don't Care | Always |
| RS9 | BODY | New | Don't Care | Don't Care | Always |

Rules for Routing Pattern *MR/CT SPINE*

| Destination | Criteria | | | | |
| --- | --- | --- | --- | --- | --- |
| | Specialty | Study Status | Referring Physician | Patient Location | Arrival Time |
| RS9 | NEURO | New | Don't Care | Don't Care | Always |

Rules for Routing Pattern *PORTCHEST*

| Destination | Criteria | | | | |
| --- | --- | --- | --- | --- | --- |
| | Specialty | Study Status | Referring Physician | Patient Location | Arrival Time |
| RS3 | CHEST | New | Don't Care | Don't Care | Always |
| RS1 | CHEST | New | Don't Care | Don't Care | At Night |

FIG. 9

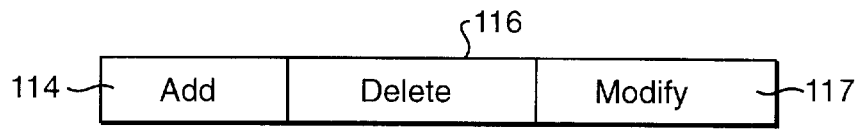

2. *Click on Add or Modify and enter the information:*

Modify Rule

Select the specialty and modality for this rule:

| | |
|---|---|
| Specialty | [Select a specialty or "Any"] |
| Modality | [Select the modality or "Any"] |

Select the pre-fetch rule options:

| | |
|---|---|
| Fetch same specialty | [YES or NO] |
| Fetch same specialty | [YES or NO] |
| Maximum number of studies to fetch | [Enter a number*] |
| Oldest study to fetch | [Enter a number] in years |
| Fetch the oldest study | [NO or YES] |
| Fetch summary (if present) | [YES or NO] |
| Fetch only the summary | [NO or YES] |
| Route priors | [YES or NO] |
| Cache priors | [YES] |

(115 braces Modality through Fetch same specialty)

4. *Add or modify the rule by clicking Update*

FIG. 11

| Patient Name | Accn # | Pat ID | Study ID | Date | Exam Code | Images | Status | | MOD | Station |
|---|---|---|---|---|---|---|---|---|---|---|
| PATIENT720 | 1202574 | 892259 | 17680 | 12/04/97 | CDAC | 65 | L | NT | CT | Picker CT |
| PATIENT642 | 1150200 | 9398351 | 16081 | 11/02/97 | CTAP | 66 | L | PN | CT | CT01080 |
| PATIENT270 | 81480 | 98746 | 70731 | 08/23/98 | CTPP | 60 | L | N | CT | Passport |
| PATIENT278 | 760348 | 32124 | 6563 | 01/05/90 | CTAB | 95 | L | N | CT | DT01080 |
| PATIENT263 | 78609 | 361581 | 7344 | 01/02/98 | CTAP | 57 | L | N | CT | |
| PATIENT278 | 767687 | 32124 | 6477 | 12/29/95 | CTAPOD | 62 | L | N | CT | CT02000 |

FIG. 12

| | | |
|---|---|---|
| Patient ID | 775105 | |
| Name | HIDDEN | |
| Sex | F | |
| Location | ICU | |
| Study ID | 1041136 | |
| Date | 01/24/97 | |
| Time | 08:45:29 | |
| Stat Inq. | ADC DI6I | |
| Accession number | 1043136 | |
| Procedure | PCH2 | |
| Modality | | |
| Physician | | |
| Reported Status | New Study | |
| Study Status | Closed | |
| Speciality | BODY | |
| Private Field | | |
| Study Comments | You may apply a keyword to this ---- ----- the pull-down to the lower right corner of this form. It is then possible to --- | |
| Study Reason | | |
| Study Keywords | lung cancer | ☐ ☐ Lung cancer |

FIG. 13

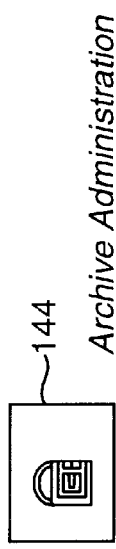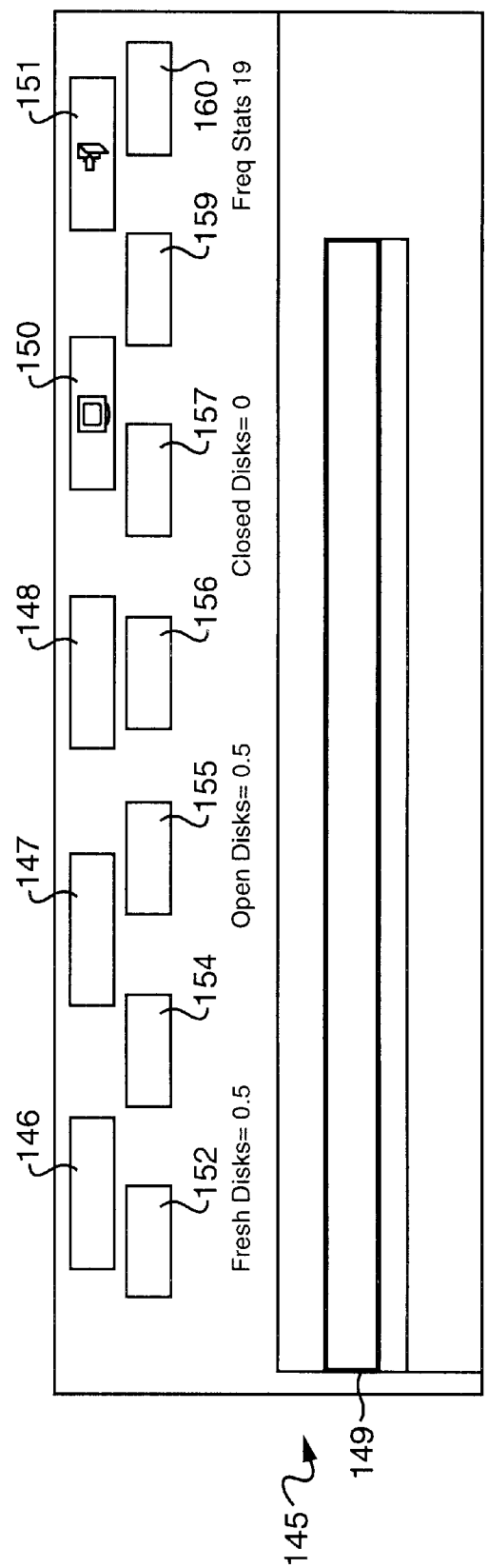
FIG. 14

FIG. 15

|  |  |  |
|---|---|---|
| 👓 | ▫ | ⬚ |

| | |
|---:|:---|
| Patient ID | |
| Name | |
| Sex | Any |
| Location | |
| Accession number | |
| Procedure | CHPORT |
| Ref. Physician | |
| Specialty | CHEST |
| Keywords | Lung Cancer |
| Date | From 11 27 1997<br>To 12 31 1997 |
| Station | |
| Study ID | |

Any modality | Any status | System

FIG. 16

PICTURE ARCHIVING AND COMMUNICATION SYSTEM

BACKGROUND OF THE INVENTION

1. Field of the Invention

The present invention is directed to a picture archiving and communication system which includes improved image routing, retrieval and display capabilities, among other things. The invention has particular utility in a hospital, or group of hospitals, since it facilitates inter-departmental access to patient images produced by different types of imaging modalities.

2. Description of the Related Art

Modern hospitals, like any other business, make use of digital computers and networking technology to manage different types of data. Much of this data, such as admissions information and the like, can be handled without the use of specialized hardware and software. On the other hand, certain types of clinical data, in particular medical images, cannot be managed in the conventional manner. Rather, specialized hardware and software is required to route, retrieve and view this data. This specialized hardware and software is known in the art as a picture archiving and communication system (or "PACS").

In general, a PACS includes one or more imaging modalities, an archive, and plural reviewing stations. The imaging modalities take images of a patient using technologies such as X-ray, computed tomography ("CT"), magnetic resonance imaging ("MRI"), nuclear medicine ("NM"), and ultrasound ("US"), to name a few. The images are then stored in the archive, from which they may be subsequently retrieved and viewed on a reviewing station. The imaging modalities, the archive, and reviewing stations are typically integrated either via a local area network ("LAN") or a wide area network ("WAN").

Conventional PACS suffer from several drawbacks, particularly in the areas of routing, retrieving and displaying images. With respect to image routing, in conventional PACS, an imaging modality takes an image of a patient and then the image is routed to an archive, where it is stored. Thereafter, a user at a reviewing station must retrieve the image from the archive in order to view the image. This system is inefficient for a number of reasons. For example, it requires the user to retrieve images manually, and thereby expend extra time and effort to complete the review process. In this regard, when the PACS network is busy, different users often compete for system resources, resulting in a slow system response and thereby further increasing the time required to complete the review process.

With respect to image retrieval, as noted above, conventional PACS require a user to retrieve an image from a central archive. This can be inefficient, especially if a copy of the image is located in an area of the PACS which is more easily accessible to the user than the archive. Moreover, when dealing with "studies" (i.e., one or more images of, e.g., a body part of a patient), conventional PACS retrieve an entire study before any images therefrom are actually displayed to the user. Again, this is inefficient, since it prolongs the reviewing process.

With respect to displaying images, conventional PACS typically provide a fixed set of controls by which a user may sort, select and display certain studies and/or images. While these controls may be sufficient in some circumstances, oftentimes users will find them inadequate to meet their particular needs. On the other hand, this fixed set of controls may also be more than the user desires and/or may have characteristics, such as an undesirable screen location or the like, that the user finds inconvenient.

Accordingly, there exists a need for a PACS which addresses the foregoing and other drawbacks of conventional PACS. In particular, there exists a need for a PACS with improved routing, retrieval and display capabilities which enhance the overall efficiency of the system, and which make the system more user-friendly.

SUMMARY OF THE INVENTION

The present invention addresses the foregoing needs. In particular, the present invention is a PACS with routing, retrieval and display capabilities that surpass those of its conventional counterparts, and with additional enhancements and features that make the subject PACS both efficient and user-friendly.

Generally speaking, the PACS of the present invention includes core components arranged in a cluster. These core components include an archive station which has access to a long-term memory for storing image data, and a reviewing station which has a display for displaying images based on received image data. Also included in the core components is a network gateway, which interfaces to a non-core component so as to receive image data therefrom, and which routes the image data to at least one of the archive station and the reviewing station based on a set of routing rules in the network gateway. Finally, a database server manages access to the image data, and stores information relating to the image data.

According to one aspect, the PACS includes a plurality of reviewing stations, each which is designated to receive images based on predetermined routing rules. In this aspect, the network gateway receives the images from an external source, determines, which if any, of the reviewing stations that each image should be routed to based on the predetermined routing rules, and routes images to appropriate reviewing stations. By routing the images to appropriate stations, rather than blindly routing all images to a central archive (as is done in conventional PACS), the present invention reduces the amount of time it takes for users to access and view the images.

In preferred embodiments, the invention determines the routing rules based on one or more of the following: a set destination, a radiology specialty, image status, a referring physician, patient location, time, image category, and imaging modality. Moreover, the invention provides a way for the user to set the routing rules by selecting one or more of the foregoing options, thereby enabling the user to generate customized routing tailored to specific needs. In particularly preferred embodiments, the user selects the above options using one or more forms which are accessible via hyperlinks. This feature, in particular, makes the PACS easy to use.

In other preferred embodiments, the network gateway is able to determine if received images and their corresponding information comport with what is already stored in the PACS. Specifically, the network gateway determines if any received images include additional information that is inconsistent with corresponding information on the PACS, and corrects the additional information in any such received images prior to routing the images. Thus, the network gateway both prevents flawed (i.e., "broken") images from entering the PACS and/or from corrupting currently-existing PACS data. This feature is particularly advantageous in the medical field, where data accuracy can literally mean the difference between life and death.

In still other preferred embodiments, the network gateway is able to route images to a plurality of other (e.g., non-reviewing) stations in accordance with predetermined routing rules. Examples of these other stations include the archive station and PACS extensions (i.e., non-core components), most notably a referring physician station which displays images received from the network gateway and a clinical station which also displays such images. Similarly, the network gateway may also route images to peripherals, such as a Web server which sends the images out over the Internet and a printer which prints the images.

According to another aspect, the PACS pre-fetches images (and/or summaries of information relating to the images) in response to a scheduled event. In this regard, "pre-fetching" refers to the process of automatically (i.e., without user intervention) retrieving images (and/or summaries) before the scheduled event. In this aspect, the PACS includes at least one station capable of displaying the images, and a network gateway which communicates with the station and a remote source (e.g., a hospital radiology information system, or "RIS"). The network gateway receives information concerning the scheduled event from the remote source, queries the remote source for details on the scheduled event, receives the details from the remote source, and retrieves images (and/or summaries) from a memory on the PACS based on the details and one or more predetermined pre-fetching rules. By effecting pre-fetching in this manner, the invention further reduces the amount of time required to review images. That is, because the images and/or summaries have been pre-fetched, they will be ready and waiting for the reviewer (e.g., a physician) at the time of the exam. With regard to the summaries, retrieval of the summaries only is a significant advantage, since it eliminates the need to retrieve an image when only its summary is needed.

In some embodiments of the invention, e.g., in a case that the station noted above has its own internal cache, the network gateway may route the retrieved images directly to the station. In other embodiments, however, most notably the case where the station is cache-less, the network gateway stores the retrieved images in memory (e.g., a cache on an archive station), and waits for a request from the reviewing station before routing the retrieved images thereto. By providing this flexibility, the PACS can be implemented using either "cached" or cache-less reviewing stations, depending upon the PACS users' available hardware, preferences and/or needs.

According to another aspect, the invention is a workstation (e.g., a PACS core component or a PACS extension) which effects pipeline image retrieval in accordance with the present invention. The workstation does this by retrieving images from one or more caches located in different components of the PACS, rather than always retrieving the images from a central archive as is done in conventional systems. The workstation includes a display screen capable of displaying images and one or more memories which store computer-executable process steps and a list of studies, each of which is comprised of one or more images. A processor in the workstation executes the process steps in order to retrieve image data for designated studies in the study list and to form images on the display screen using the image data. These process steps include code to select caches of one or more different PACS components, to retrieve image data for designated studies from caches of the selected components, to form each image in the studies from retrieved image data, and to display each image on the display screen once the image is formed, without waiting for image data for any additional image data to arrive.

The foregoing aspect of the invention takes advantage of the fact that images in PACS component caches may be more accessible than those on the archive may be. Thus, by permitting retrieval of image data from caches, rather than requiring that image data be retrieved from the archive (as is the case in the invention's conventional counterparts), the invention reduces image retrieval time, and thus increases the system's efficiency. Moreover, the invention saves additional time by displaying individual images of image data, rather than waiting until image data for a full study has been received.

In preferred embodiments, the caches of the different PACS components are selected based on a user input. For example, the workstation may display a user interface which includes a list of studies, at least one of which has a "cached" status designation associated therewith. The user input in this case comprises simply selecting at least one of the studies in the list which has the "cached" status designation associated therewith, whereafter the workstation identifies the cache by correlating it with the selected study. Of course, selection can also be made automatic, e.g., by including code in the workstation to seek out all studies in the list with a "cached" status designation, and then selecting caches associated with those studies.

According to still another aspect, the PACS includes a workstation which generates a user-customized PACS display (e.g., a main study list, worklist, display toolbar, etc.). The workstation includes a memory and a processor which executes stored process steps in order to invoke display of at least one form (e.g., a user profile form) which includes settable options for altering the PACS display, to store user inputs to the form which correspond to the settable options, and to generate the user-customized PACS display based, at least in part, on the user inputs to the form. Thus, with respect to the PACS display, the invention is more flexible, and thus more user-friendly, than its conventional counterparts.

In some embodiments of the invention, the PACS display comprises a list of studies (e.g., a main study list), each of which includes one or more images, and a plurality of action buttons. In these embodiments, the above form includes options to select which action buttons appear on the PACS display. An additional form (e.g., an access control form) may also be invoked to provide the user with the ability to customize the PACS display even further.

In other embodiments, the PACS display comprises a toolbar that is displayed concurrently with medical images. The toolbar includes a plurality of action buttons which affect image display. In these embodiments, the form includes options affecting where on the display screen the tool bar is displayed and a format of the toolbar, in addition to options for selecting which action buttons will be displayed in the toolbar.

In particularly preferred embodiments, the PACS display (e.g., the toolbar) includes action buttons for manipulating displayed images. Among the action buttons which may be included on the toolbar are an action button to collimate displayed images, an action button to affect the orientation of displayed images, an action button for re-ordering displayed images, action buttons for dynamically displaying images, action buttons particularly for use with CT images, and action buttons for adding information to displayed images. These features (and others listed below) provide PACS users with enhanced control over image editing and viewing, and with a variety of useful tools which heretofore have been unavailable in PACS.

This brief summary has been provided so that the nature of the invention may be understood quickly. A more complete understanding of the invention can be obtained by reference to the following detailed description of the preferred embodiment thereof in connection with the attached drawings.

BRIEF DESCRIPTION OF THE DRAWINGS

FIG. 6 shows a form which allows a user to set various PACS stations as potential recipients of routed studies.

FIG. 8 shows a form for creating routing rules/patterns.

FIG. 9 shows a different version of a form for creating routing rules/patterns.

FIG. 11 shows a form for creating pre-fetching rules.

FIG. 12 shows a main study window used in the PACS.

FIG. 13 hows a study information form.

FIG. 14 shows an archive administration form.

FIG. 15 shows a "fixup" graphical user interface.

FIG. 16 shows a custom query form.

DETAILED DESCRIPTION OF THE PREFERRED EMBODIMENT

Figure 1:
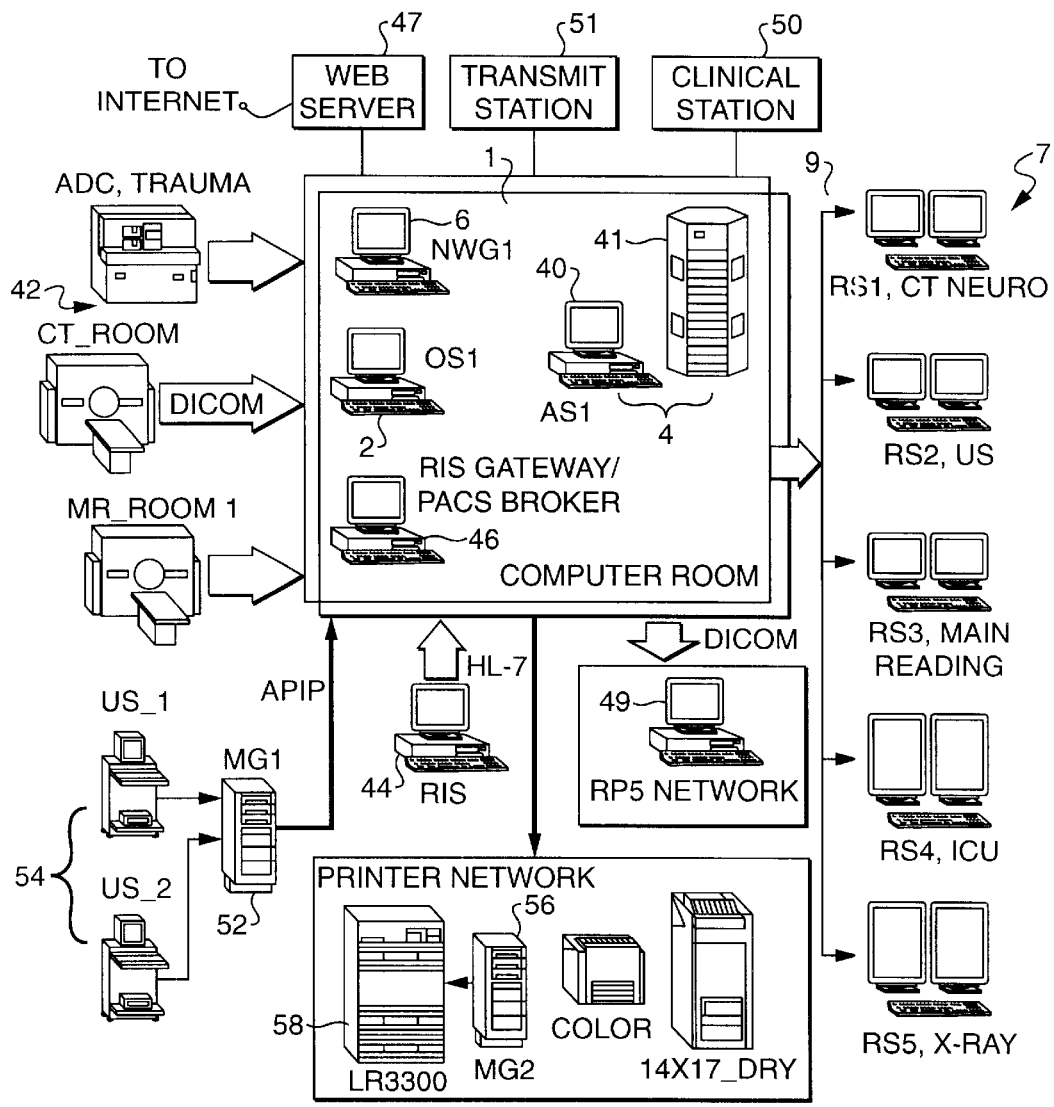
FIG. 1 shows an overview of a representative PACS in accordance with the present invention.

The PACS invention described herein is preferably implemented via a DICOM 3.0 ("Digital Imaging and Communication in Medicine") compliant, high-speed, networked computer system designed for digital storage, routing, retrieval, transmission, display and printing of medical images. In this regard, DICOM is an industry-standard communications protocol for the exchange of medical images and information between computers and computing peripherals. See Horiil, et al., "DICOM: An Introduction to the Standard", http://www.xray.hmc.psu.edu/dicom/dicom_home.html/DICOMIntro.html (Sep. 1, 1998). Preferred embodiments of the invention also maintain backward compatibility with ACR-NEMA (DICOM 2.X) protocols, permitting integration of legacy non-DICOM 3.0 imaging modalities into the invention.

The invention can be used in a variety of environments, ranging from out-patient teleradiology spokes, to large hospitals and teaching institutions, to associations thereof linked via a WAN or the Internet. Preferred embodiments thereof use a modular, scaleable, and expandable hardware architecture to meet the present and future needs of users (e.g., radiology professionals) over a wide range of diagnostic and clinical applications. DICOM 3.0 compliant modular application software ensures operability with DICOM imaging modalities, LAN/WAN connectivity over standard TCP/IP network topology, and smooth integration with pre-existing PACS infrastructures.

1.0 Hardware

The PACS described herein is organized by cluster, with each cluster comprising a set of core components that fall under the domain of one database server instance. Preferred embodiments of the invention utilize an Oracle® database server, with the remaining core components comprising Sun® Enterprise workstations running the UNIX-based Sun® Solaris 2.5.1 operating system. Of course, the core components are not limited to these hardware and software platforms, meaning that they can comprise any type of appropriate computing equipment. A brief listing and description of the core components is provided below in Table 1.

TABLE 1

PACS Core Components

| Core Component | Role in PACS |
|---|---|
| Archive Station ("AS") | Provides long-term DICOM archive for permanent storage and retrieval of studies, i.e., a digital file room. There are two types of archive stations used in the invention: a magneto optical disk ("MOD") - based station, and a digital linear tape ("DLT") - based station. |
| Network Gateway ("NWG") | Performs DICOM validation and print services, network compression, radiology information system ("RIS") validation, AGFA ® PACS Interface Protocol ("APIP") translation, and workflow automation, including routing, pre-fetching of prior relevant patient images, and generation of user-defined demographic overlays. |
| Database Server ("OS") | Manages and shares information related to study attributes, system configuration, user accounts, study mark-up, and annotation. |
| Review Station ("RS") | Comprises full-featured, multi-modality, dual monitor diagnostic and clinical display stations with access to the archive station and an RIS report database. |

FIG. 1 shows a typical PACS cluster in accordance with the present invention. Specifically, core PACS cluster 1 includes a database server 2, one or more archive stations 4, and one or more network gateways 6 located in a secure, air-conditioned computer room, with one or more reviewing stations 7 spread throughout the facility (e.g., the hospital) and connected to the remaining core components by a fast switched TCP/IP network 9. Each of these core components is loaded with appropriate PACS software modules to effect specific PACS functions. Because of the modular design of this software, it is possible to combine several PACS software modules in one workstation, and thereby provide a workstation that handles, e.g., both the archiving and network gateway functions. However, for the sake of clarity, the invention is described using a separate workstation for each function. As also shown, additional PACS components, called "extensions", may be interfaced to the core components to effect various functionalities, as described below in section 1.6.

1.1 Workstation Hardware

Figure 2:
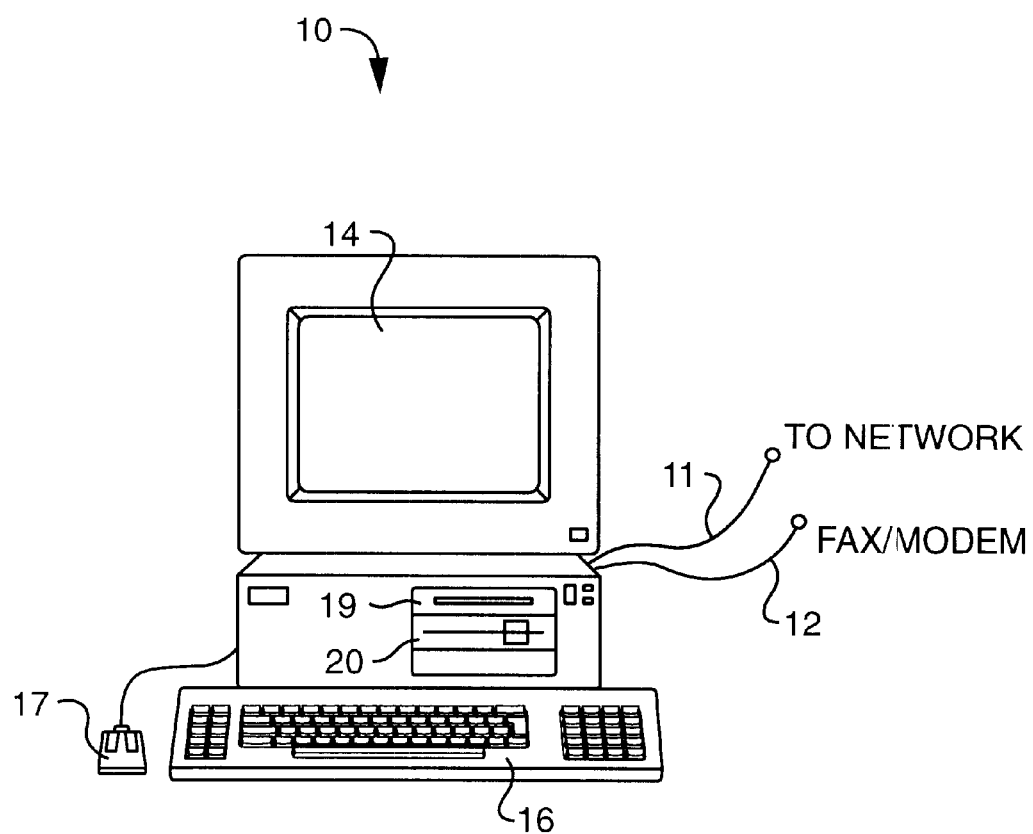
FIG. 2 shows generalized hardware for "workstation" components of the PACS shown in FIG. 1.

FIG. 2 shows a general hardware configuration for each PACS core component and extension noted above. Of course, each of the core components and extensions includes specific software, and may include additional hardware, for performing its unique function. In addition, certain extensions, such as a printer, are clearly not defined by the hardware shown in FIG. 2. However, each PACS station that can be implemented by a workstation, or personal computer ("PC"), preferably has the following features shown in FIG. 2. Therefore, a general discussion of these features is provided here, followed below by detailed descriptions of additional hardware and software for each PACS component/extension.

As shown in the figure, workstation 10 includes one or more network connections 11 for interfacing to a network, such as the PACS DICOM network and the Internet, and one or more fax/modem connections 12 for interfacing with other remote sources. Workstation 10 also includes one or more display screens 14 for displaying information to a user, keyboard 16 for inputting text and user commands, and mouse 17 for positioning a cursor on display screen 14 and for inputting user commands. Workstation 10 may also include disk drive 19 for reading from and writing to floppy disks installed therein, and CD-ROM drive 20 for accessing information stored on CD-ROM.

Figure 3:
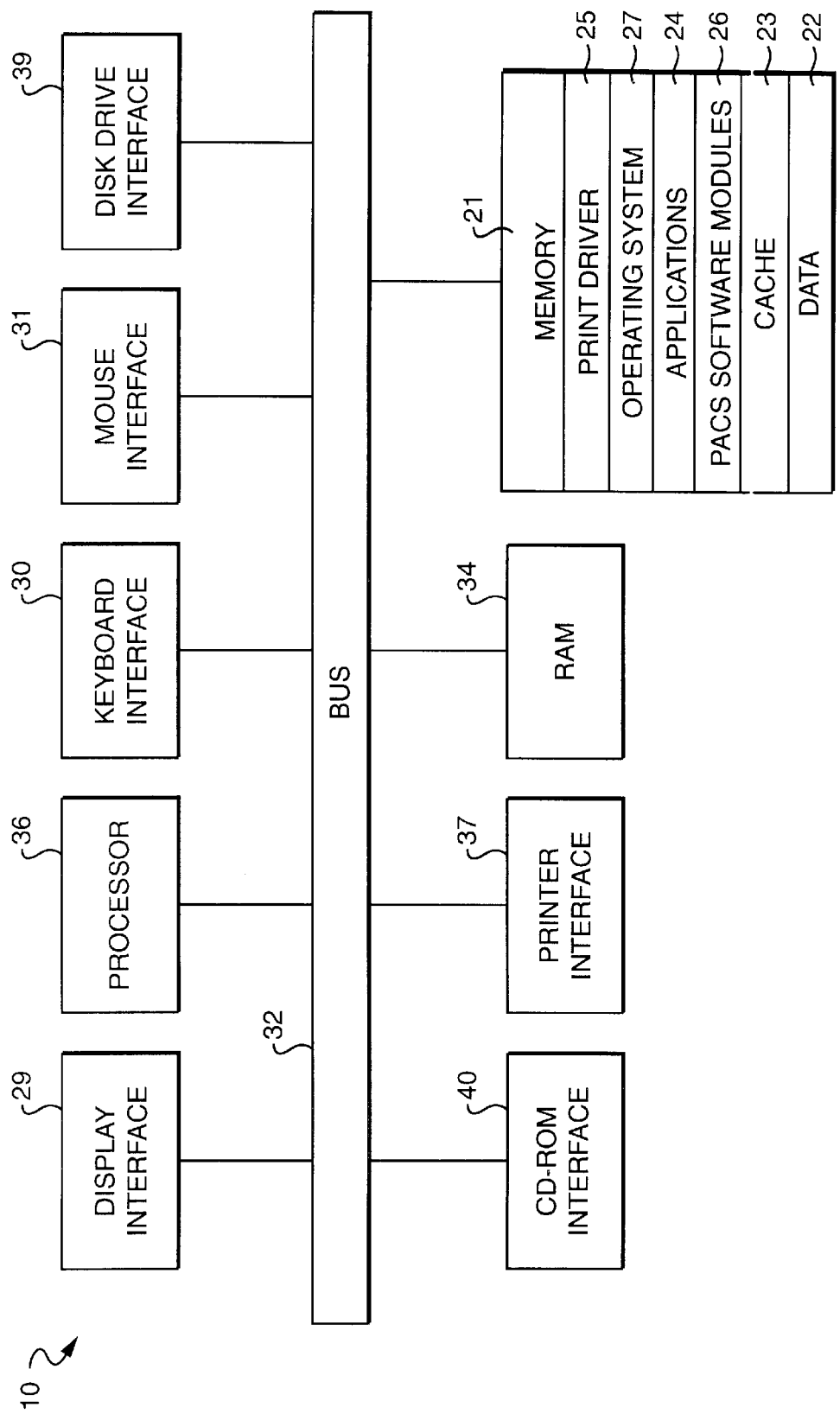
FIG. 3 shows a generalized architecture for the hardware shown in FIG. 2.

FIG. 3 shows the internal architecture of workstation 10. As shown in FIG. 3, workstation 10 includes memory 21, which comprises a computer-readable medium such as one or more computer hard disks. A portion of memory 21 may comprise a cache 23 for the workstation. In addition, memory 21 stores data 22, applications 24, print driver 25, PACS software modules 26, and an operating system 27. The applications and operating system of each workstation varies for each PACS component, as described below. At least some of PACS software modules 26, however, are included on each PACS component in order to effect the storage, routing, retrieval, transmission, display, and printing of medical (or other) images described herein. Generally speaking, these PACS software modules comprise computer-executable code that defines process steps for effecting the various PACS functions of each component/extension. In this regard, it is noted that since each PACS component/extension does not need to perform all PACS functions, it is generally not necessary to load all of the PACS software modules onto each component/extension. Rather, only those modules needed to effect the specific functionality of that component/extension need be loaded. As noted above, however, modules for performing different PACS functions (e.g., archiving and network gateway functions) may be loaded into the same workstation, if desired.

Also included in workstation 10 are display interface 29, keyboard interface 30, mouse interface 31, computer bus 32, RAM 34, processor 36, printer interface 37, and possibly disk drive interface 39 and CD-ROM drive interface 40. Processor 36 comprises a microprocessor (the type of which varies depending upon the station, as described below) for executing the applications and PACS software modules out of RAM 34. In this regard, RAM 34 can comprise several memory devices. The applications and PACS software are preferably stored in memory 21, as noted above. Alternatively, however, applications may be stored on a floppy disk in disk drive 19 or a CD-ROM in CD-ROM drive 20. In this case, processor 36 accesses these applications (or other data) stored on a floppy disk via disk drive interface 39 and accesses applications (or other data) stored on a CD-ROM via CD-ROM drive interface 40. Application execution and other tasks of workstation 10 may be initiated using keyboard 16 or mouse 17, commands from which are transmitted to processor 36 via keyboard interface 30 and mouse interface 31, respectively. Output results from applications running on workstation 10 may be processed by display interface 29 and then displayed to a user on display 14. To this end, display interface 29 preferably comprises a display processor for forming images based on data provided by processor 36 over computer bus 32, and for outputting those images to display 14. Rather than including a separate display processor, the functionality of display processor 36 may be implemented by processor 36. Output results from the PACS software modules, e.g., medical images, may also be output to network printers, such as those described below in section 1.6.7. To this end, processor 36 executes print driver 25 which performs appropriate formatting of the output results prior to their transmission.

Local printers also may be attached to various stations, if desired, which can be accessed via printer interface 37.

1.2 Archive Station

Archive station 4 comprises a workstation 40 having a memory device 41 connected thereto. This memory device comprises central and secure near and long-term DICOM storage for studies provided from imaging modalities. In this regard, a "study" comprises a series of images captured by an imaging modality. The invention described herein can be used to manage folders of studies, individual studies, series of images, or individual images. Accordingly, henceforth, these terms can be used interchangeably.

Included on archive station 4 is software for controlling reading from, and writing to, memory device 41 in response to requests/instructions received from other core components, most notably reviewing stations 7, network gateway 6, and the extensions. The software also generates a graphical user interface ("GUI") (not shown), which provides the PACS administrator with the ability to manually control deleting, splitting and merging of studies, as well as querying, transmitting and retrieving studies. These operations are described in detail below. There are also configurable privilege level security controls on the GUI to prevent unauthorized persons from accessing archive configuration and management tools.

In preferred embodiments of the invention, original image data is stored on the archive station, and that original image data does not change, meaning that retrieved and edited images are not stored back to the archive station. Instead, edited images and the like are stored to database files on the archive station. These database files are preferably stored in a hard disk or the like on workstation 40, and comprise a collection of all information relating to studies and parameters associated with setup of the PACS. An example of information stored in the database is demographic information associated with each patient and study.

As noted in Table 1 above, the archive station may comprise either a magneto optical disk (or "MOD")—based archive station, or a digital linear tape (or "DLT")—based archive station.

1.2.1 MOD-Based Archive Station

The MOD-based archive station includes a three-tiered storage system that uses hard disks (preferably 4 giga-bytes each) for on-line data storage (usually one week's worth of data), MODs (i.e., high-capacity, removable storage media having preferable either 2.3 or 4.6 giga-bytes of storage each) for intermediate-term data storage (usually one to two years), and DLT media for long-term backup storage. Additional RAID ("Redundant Array of Inexpensive Disks") may also be provided for expanded short term storage, depending upon the storage requirements of the facility and the number of studies handled thereby. The portion of short term storage, i.e., the RAID and other hard disks, which stores images comprises the MOD-based archive's cache.

In a MOD-based archive station, the MODs themselves are housed in scalable optical disk jukeboxes. An optical disk jukebox is a mass storage device that reads data from, and writes data to, MODS (or, alternatively, to DLTs). Here, each optical disk jukebox preferably holds between 20 and 500 MODS, or up to 4 tera-bytes of memory total. Each MOD-based archive station drives one optical disk jukebox, and provides both manual and automatic control of data migration from short term storage to the MODs. With respect to manual control, the PACS administrator prepares and loads MODS into the jukebox, supports requests for off-line volumes, and periodically checks station queues using queue management and service tools provided on the archive's user interface. In preferred embodiments of the invention, the workstation also runs an "auto-pilot" routine which patrols the archive's cache and which automatically deletes studies once they have been archived on a MOD. This is done in order to prevent the cache from "overflowing". Certain studies may be protected from this auto-deletion by assigning them a "protected" status. This is described in detail below.

1.2.2 DLT-Based Archive Station

In the MOD-based archive station described above, DLT is configured to backup the primary long-term storage in order to provide data redundancy. On the other hand, in the DLT-based archive station, the DLT is used for primary intermediate and long-term storage. In preferred embodiments, DLTs having a storage capacity of 35 giga-bytes each are used; although the invention can be used with DLTs having other storage capacities as well. The DLTs are stored in scaleable DLT jukeboxes, preferably capable of holding 30/100 588 DLTs, where one workstation drives one jukebox. In addition, MODs may also be provided for additional and/or backup intermediate and long-term storage. As above, RAID and hard disks are also provided for short-term storage of studies and for database storage. The DLT-based archive station provides both manual and automatic control of data migration from short term storage to DLT. These controls are substantially similar to those described above with respect to the MOD-based archive station and, therefore, are not repeated here for the sake of brevity.

1.3 Network Gateway

Generally speaking, the network gateway is the "workflow manager" of the PACS, meaning that it receives images (as image data) from various non-core components including imaging modalities, confirms the validity of the received images, and routes them appropriately. To this end, the network gateway comprises a workstation that supports at least six, preferably more, simultaneous associations with DICOM-compliant imaging modalities. These modalities include, but are not limited to, X-ray, CT, MRI, NM and US modalities. Depending upon the number of imaging modalities, the PACS may use several network gateways in each cluster in order to provide load balancing and enhanced throughput.

As shown in FIG. 1, network gateway 6 is in communication with reviewing stations 7 and imaging modalities 42 via the DICOM network, and is in communication with remote sources, such as the hospital's RIS 44 and various other PACS extensions. The network gateway thus receives studies from one or more imaging modalities and/or from the remote sources, and provides DICOM security and validation services therefor. To this end, the network gateway preferably includes optical character recognition ("OCR") and APIP translation capabilities to accommodate non-DICOM 3.0 imaging modalities. The network gateway also controls routing of these studies to selected PACS core components and extensions, and pre-fetching and routing of relevant prior studies between the archive and reviewing stations. Rules for routing and pre-fetching studies may be based on a number of factors, as described in more detail below in section 2.

Among the other services provided by the network gateway is RIS validation. RIS validation ensures integrity of patient demographic information in the studies. To this end, the network gateway captures and stores studies in a private cache located, e.g., in a hard disk on the network gateway, so that key demographic information (e.g., patient identification, accession number, etc.) can be validated based on pre-stored information, as described in more detail below.

The network gateway also provides DICOM print management services for the PACS cluster in which it resides. To this end, the network gateway includes routines which perform JPEG network compression and 12-to-8 bit simplification to accommodate DICOM printers, third party DICOM interfaces, and referring physician software, such as RP5. Workflow extensions resident on the network gateway also allow users to generate custom demographic overlays for images/studies. Finally, the network gateway also includes comprehensive queue management and service tools, as well as configurable privilege security controls to prevent unauthorized persons from accessing the gateway's configuration tools.

1.4 Database Server

In preferred embodiments of the invention, database server 2 is an Oracle® V.7.3.X database server with RAID storage; however, it is important to note that the invention is not limited to use with this type of server. In general, the database server performs a variety of functions relating to retrieval and storage of studies located in the archive station (s). Among other things, the database server collects, organizes and manages patient and study demographic data that is contained in DICOM header files of each study. To this end, the database server stores all study attributes, including, but not limited to, image annotations and edits, window/level settings, measurements, and radiologist comments. The database server also stores all system configuration settings, including, but not limited to, user accounts, user profiles (i.e., a set of attributes associated with each login ID), preferred routings, demographic overlays, and DICOM network connectivity.

The database server keeps track of where all studies "live" at the time, meaning the current location of a study in the PACS cluster. Thus, all query, transmit, retrieve, store and print actions initiated by a client, i.e., a PACS station, go through the database server (either directly or via the network gateway). As a result, database server 6 effectively manages access to images throughout the PACS. Comprehensive queue management and service tools are provided in the database server to effect these functions. Moreover, in preferred embodiments of the invention, advanced system monitoring tools are also included in the database server, which alert the PACS administrator that service or manual intervention is required.

As a general rule, studies are not stored on the database server, unless the server also includes software modules to effect other core PACS functions. However, in most cases, the database server is a dedicated workstation with no archive or gateway functionality. Additional hardware, however, may be required to meet the facility's study volume, number of client stations, and required levels of performance and accessibility.

1.5 Reviewing Stations

Reviewing stations 7 are workstations that may be used to retrieve and to view medical images handled by the PACS, as well as information relating thereto. The reviewing stations may be located remotely from the other PACS core components; that is, either remotely inside the same building/facility or remotely at a separate geographic location. In either case, a network (e.g., LAN, WAN, or the Internet) links the reviewing stations to the other PACS core components, in particular to network gateway 6.

Each reviewing station preferably comprises a dual monitor, multi-modality, reading station with features provided by PACS software modules, including, but not limited to, window/level adjustment, image magnification, roam and zoom, and image annotation and measurement. The reviewing stations also perform automatic worklist generation and updates as relevant studies arrive. Regarding worklist generation, upon logging in to the PACS via a reviewing station, a user may enter a query asking the PACS to locate a study or group of studies based on input criteria, such as an accession number, which is a unique identifier for each study. Once these studies have been located, the PACS generates, and the reviewing station displays, a user interface called a main study window. This main study window is comprised of action buttons, system status indicators, and a main study list which includes studies that match the input criteria. The worklist comprises the study, or group of studies, that the user selects from the main study list.

The reviewing stations provide users with the ability to view one or more such selected studies in a variety of different, selectable display formats, and then to print or transmit the studies using a displayed tool bar. With regard to viewing the studies, the reviewing stations may be modality-specific as is the case in FIG. 1. Therefore, they may have modality-specific viewing options, including, but not limited to, CT scout mode, MR cursor mode, image zoom, CINE loop, and image drag and drop features, all of which are described below. The viewing options also may include the ability to display multiple studies for the same patient on a single reviewing station. Flexible controls are generally provided for navigating through the larger studies.

The invention also provides a way to customize the main study window and tool bar based on a user profile. Other options provided on the reviewing stations include the ability to access RIS reports and to create summary series folders for a patient, which summary series folders comprise selected patient images from one or more studies.

In preferred embodiments of the invention, four different types of reviewing stations may be used in the PACS; although the invention is not limited to these four. Specifically, each PACS cluster may include only one, or more than one, type of these reviewing stations. Table 2 below lists features of these reviewing stations.

TABLE 2

PACS Reviewing Stations

| Designation | Application | Hardware Platform | Monitors |
|---|---|---|---|
| RS5000 | De-configured clinical review (plain film) | Sun ® Ultra 1, 170 | 1280 × 1024 monochrome |
| RS3000 | CT/MR/TO radiology primary reading | Sun ® Ultra 2, 1200 | 1280 × 1024 Hi-bright monochrome |
| RS3000 Color | US/NM radiology primary reading | Sun ® Ultra 1, 1200 | 1280 × 1024 Hi-res color |
| RS3000 2K Portrait | CR/CT/TO radiology primary reading | Sun ® Ultra 2, 1200 | 2048 × 2560 Hi-bright monochrome |

Each reviewing station may include a hard disk, RAID, or the like, which acts as its local cache. In reviewing stations of this type, prior to display, images are loaded into the cache, and then later retrieved at display time. Alternatively, the invention may operate with cache-less reviewing stations. In this case, images are routed to the reviewing stations when they are to be displayed, rather than being stored in the reviewing station's cache. In this regard, in the present invention, the images are generally routed from a cache in the archive station or the network gateway. Advantages of using cache-less reviewing stations include reduced network overhead and reduced memory capacity in, and thus reduced cost of, the reviewing stations. In other respects, cache-less reviewing stations behave similarly to their "cached" counterparts, except that they do not use a DICOM retrieve process, and the is PACS does not route or pre-fetch studies to a cache-less reviewing station. Routing and pre-fetching are described in detail below.

1.6 PACS Extensions

As shown in FIG. 1, in addition to the core components described above, the PACS may include one or more extensions. These extensions provide added functionality to the system. For example, extensions exist which provide connectivity to a hospital's information system ("HIS") (i.e., the hospital's computer information system that integrates lab results, billing, and inventory) via the RIS. Extensions also exist which provide, among other things, low-cost referring physician display, DICOM printing, and translation services for non-DICOM 3.0 imaging modalities. In general, PACS extensions exist as stand-alone entities outside the cluster of core PACS components, and are not clients of database server 2. With one exception, namely the medical gateway described below, communication between the core components and the extensions preferably occurs through DICOM 3.0 "transmit/query/retrieve/store/print" protocols.

1.6.1 PACS Broker

PACS broker 46, also referred to herein as the RIS gateway, provides an orderly, unified view of RIS 44 to the PACS core components, referring physician or clinical stations, a diagnostic center (e.g., the AGFA® Diagnostic Center, or "ADC"), and a transmitting station. Specifically, PACS broker 46 is a stand-alone platform that listens to the RIS and responds to query/retrieve statements from the PACS core components by accessing appropriate data from the RIS. To this end, PACS broker 46 is able to communicate in HL-7 ("Health Level 7") with the RIS, and to communicate in DICOM with network gateway 6. Thus, the PACS broker makes patient demographics, schedules, study parameters, and reports on the RIS available to the core PACS components. A PACS broker, or its equivalent, is therefore generally used if image/study routing is to be performed by the network gateway based on referring physician or patient location. Moreover, the PAC broker can be programmed to update patient information in the core components periodically, thereby ensuring that the PACS has the latest patient information available.

In preferred embodiments of the invention, the PACS broker comprises a workstation which includes a color monitor and which runs Windows® NT. The workstation also preferably includes a disk drive which is at least 9 giga-bytes in size, for storing RIS reports, among other things. The PACS broker is interposed between the RIS and the network gateway, as shown in FIG. 1, and, in preferred embodiments of the invention, is connected to each via a TCP/IP network connection or the like. Of course, the invention is not limited to using this hardware to implement the PACS broker; any suitable computing equipment will do.

1.6.2 Web Server

As noted above, one of the advantages of the present invention is the ability to access images/studies from remote locations, such as over the Internet. To this end, the present invention provides Web server 47 for making information on the Internet available to the PACS, and vice versa. Of course, standard security protocols are provided in Web server 47 to prevent unauthorized persons from gaining access to information stored on the PACS.

In preferred embodiments of the invention, Web server 47 is a 100% JAVA server that provides a "no plug-in" solution for client viewing. In these embodiments, Web server 47 uses Sun® Ultra 2200 as its hardware platform, and supports 200 or more clients. Using this hardware platform, up to 50 clients may access the server concurrently. These clients may be any PC or Sun® workstation running a Hot JAVA browser or Netscape® Communicator.

Web server 47 can be configured as a client of database server 2 (i.e., as a core component) or as a stand-alone system (i.e., as an extension). In either case, in response to a request from the PACS or the Internet, Web server 47 retrieves studies (or other information) from either the PACS or from the Internet in accordance with the request. The Web server then places those studies (or other information) into its cache, which is preferably scaleable to meet the storage needs of the system. Web server 47 may then provide either full-size images of those studies or thumbnail sketches thereof to the requester. Storing the images on the Web server in FlashPix® format (developed by the Digital Imaging Group) is one way for the Web server to provide ready access to either thumbnail or full-size images.

In the case of data going out to the Internet, Web server 47 performs progressive wavelet compression on the data before it is transmitted. In a case that the Web server receives compressed data from the Internet, it performs progressive wavelet decompression prior to transmission to the PACS. The invention, of course, can support compression and decompression methods in addition to these. Using compressed data enables the Web server to support almost any type of network connection to the PACS core components including, but not limited to, LAN, WAN, POTS, ISDN, etc. Moreover, it speeds up data transmission time.

1.6.3 Referring Physician Station

Referring physician stations are loaded with RP5, and generally comprise single monitor workstations designed for referring physicians home/office use (as opposed to primary viewing). In this regard, RP5 software comprises PC-based DICOM "query/retrieve/display/report/print" software that can be loaded onto any suitably equipped workstation. Version 1.X of RP5 is a 16-bit application which runs on a variety of operating systems including Windows95® and Windows® 3.11. Version 2.X of RP5 is a 32-bit application that runs on Windows95® and Windows® NT. The 2.X version of RP5 is preferred, since it has an improved user interface and image processing enhancements, including JPEG compression.

A preferred hardware configuration for the referring physician station 49 comprises a Dell PC with a Pentium Pro 200 MHz processor, Windows® NT operating system, 64 mega-bytes of RAM, 3.1 giga-byte hard drive, 12X CD-ROM, and 33.6 KHz modem. The referring physician station may be connected to the PACS core components, in particular to the network gateway, via any type of network connection; although ISDN network connections are preferred for teleradiology applications.

In preferred embodiments of the invention, the referring physician station is not a client of database server 2, but rather includes its own database. In operation, the referring physician station uses RP5 to request and retrieve studies on the PACS. These studies are then displayed on the station. In general, the PACS only sends to the referring physician station studies or, alternatively, summaries of studies that are simplified and/or JPEG compressed. That is, in general, the referring physician station does not transmit studies back to the PACS; although RP5 can be configured to do so if this functionality is desired.

1.6.4 Clinical Station

Clinical stations are loaded with CS500 software, and generally comprise single monitor workstations designed for use by clinicians and referring physicians, and for home/office use (as opposed to primary viewing). CS500 software comprises PC-based DICOM "query/retrieve/display/report/print " software which can be loaded onto any suitably equipped workstation. CS500 has all of the functionality of the RP5 software described above, with the addition of split screen comparison of two (or more) studies, selectable inverse video, auto-pilot processes, enhanced DICOM printing tools, and login security similar to the PACS itself. Other features include linear and angular measurements of study images, balloon help tips, and support for 1280×1024 dpi and higher display resolutions.

A preferred hardware configuration for clinical station 50 comprises a Dell PC with a Pentium Pro 233 MHz processor, Windows® NT operating system (although Windows95® may be used), 64 mega-bytes of RAM, 3.1 giga-byte hard drive, 24X CD-ROM, 33.6 KHz modem, and 10/100 MB Ethernet connection. As above, the clinical station may be connected to the PACS core components, in particular to the network gateway, via any type of network connection; although ISDN network connections are preferred for teleradiology applications.

In preferred embodiments of the invention, the clinical station is not a client of database server 2, but rather includes its own database. It does, however, inherit the login names and security profiles from the PACS to which it is networked. In operation, the clinical station uses CS500 to request and retrieve studies on the PACS. These studies are then displayed on the clinical station. In general, the PACS only sends to the clinical station studies or, alternatively, summaries of studies that are simplified and/or JPEG compressed. That is, in general, the clinical station does not transmit studies back to the PACS; although CS500 can be configured to do so if this functionality is desired.

1.6.5 Transmit Station

Transmit station 51 comprises a computerized scanner which scans in film, in particular radiographic film such as X-rays, and which transmits the scanned film images to the PACS (specifically, to the network gateway) via a network (i.e., LAN/WAN) connection. In this respect, the transmit station operates in roughly the same manner as any other imaging modality on the PACS. The scanned images are transmitted to the PACS using DICOM 3.0 protocol, and may be compressed using JPEG prior to transmission. In preferred embodiments of the invention, the transmit station also organizes scanned images into patient folders (comprised of one or more studies) prior to their transmission, and can retrieve and display RIS reports from the PACS in cases where there is a PACS broker extension present.

In preferred embodiments of the invention, the transmit station is comprised of a film digitizer and a Pentium Pro PC running Windows® NT 4.1. The film digitizer is preferably capable of scanning film ranging from 8"×10" to 14"×17". Different scanning resolutions also may be provided, i.e., 512×512 through 2048×2048, together with the ability to view and rotate digitized images prior to transmission.

1.6.6 Medical Gateway

Generally speaking, a medical gateway is a programmable secondary capture device for non-DICOM 3.0 imaging modalities and output devices. The medical gateway is used to provide connectivity between these modalities/devices and the PACS. To this end, medical gateways communicate with the core PACS components via APIP, or its equivalent. In general, each medical gateway can support up to three imaging modalities or output devices, as shown, e.g., in FIG. 1. That is, in the figure, medical gateway 52 ("MG") is interposed between the PACS core components and two imaging modalities 54, and medical gateway 56 is interposed between the PACS core components and printer 58 in the printer network. In preferred embodiments of the invention, these medical gateways are PCs that are TCP/IP-ready, and that have IP routing capabilities.

1.6.7 Printers

Various DICOM-compliant printers may be connected to the PACS, as shown in FIG. 1. These printers are typically connected to the network gateway via a TCP/IP network connection; although other network connections are possible. Examples of two such printers are the Drystar® 2000 Thermal Printer and the Drystar® 3000 Thermal Printer, both of which provide at least 300 dpi in resolution.

2.0 Routing

As described above, the PACS receives studies from one or more sources. Each of these studies is routed by network gateway 6 to one or more of the stations described above in section 1, or alternatively to an output device such as a Web server or printer. To effect this routing, the network gateway executes PACS software modules in order to receive the images, to determine where on the PACS that each study/image should be routed based on predetermined routing rules, and to route the studies directly to the appropriate location automatically.

In more detail, network gateway 6 routes studies directly to a station, such as a reviewing station, an archive station, a referring physician station, a clinical station, etc., or directly to another location on the DICOM network, such as a Web server or a printer (if available), based on routing rules defined by a combination of one or more of the routing attributes set forth below in Table 3.

TABLE 3

Routing Attributes

| Attribute | Function | RIS Gateway? |
|---|---|---|
| Acquiring Station | The acquiring station is the imaging modality that sends studies to the PACS. The simplest routing scheme is one that sends all studies from one acquiring station to one or more reviewing stations. | No |
| Radiology Specialty | The PACS administrator designates certain reviewing stations for reading studies related to certain specialties (e.g., head, abdomen, pediatrics). All such studies are routed thereto. | Yes |
| Patient Location | The RIS maintains a list of patient locations that is essentially a road-map to each bed in the hospital. Reviewing stations are located in a physical space that maps to some patient location number. For example, it is possible to create routes to trauma centers, ICU, and emergency rooms using the patient location as the routing criteria. Patient location routes support wildcards (e.g., "trauma !"). | Yes |
| Referring Physician | The RIS maintains a list of referring physician names, and assigns code numbers to the names. Referring physician routes support wild cards. | Yes |
| Time | A section called "Off Peak Schedules" allows the user to configure time ranges for use as routing criteria. For example, a route could be configured to send studies to a station where an on-call physician is seated during evening hours. Another example might be to route studies to a physician's home after-hours or on weekends. | No |
| Study Status | Routing may be configured so that studies are sent to certain locations based on a change in study status. For example, the user may delay transmission of studies to clinician stations until a report has been generated. | Yes |
| Pre-fetch Rules | Selected stations may he configured as "pre-fetching" targets, while others may be excluded from pre-fetching. | Yes |

Of course, the invention is not limited to routing images based on the attributes set forth in Table 3. Other attributes also may be used as well.

Figure 4:
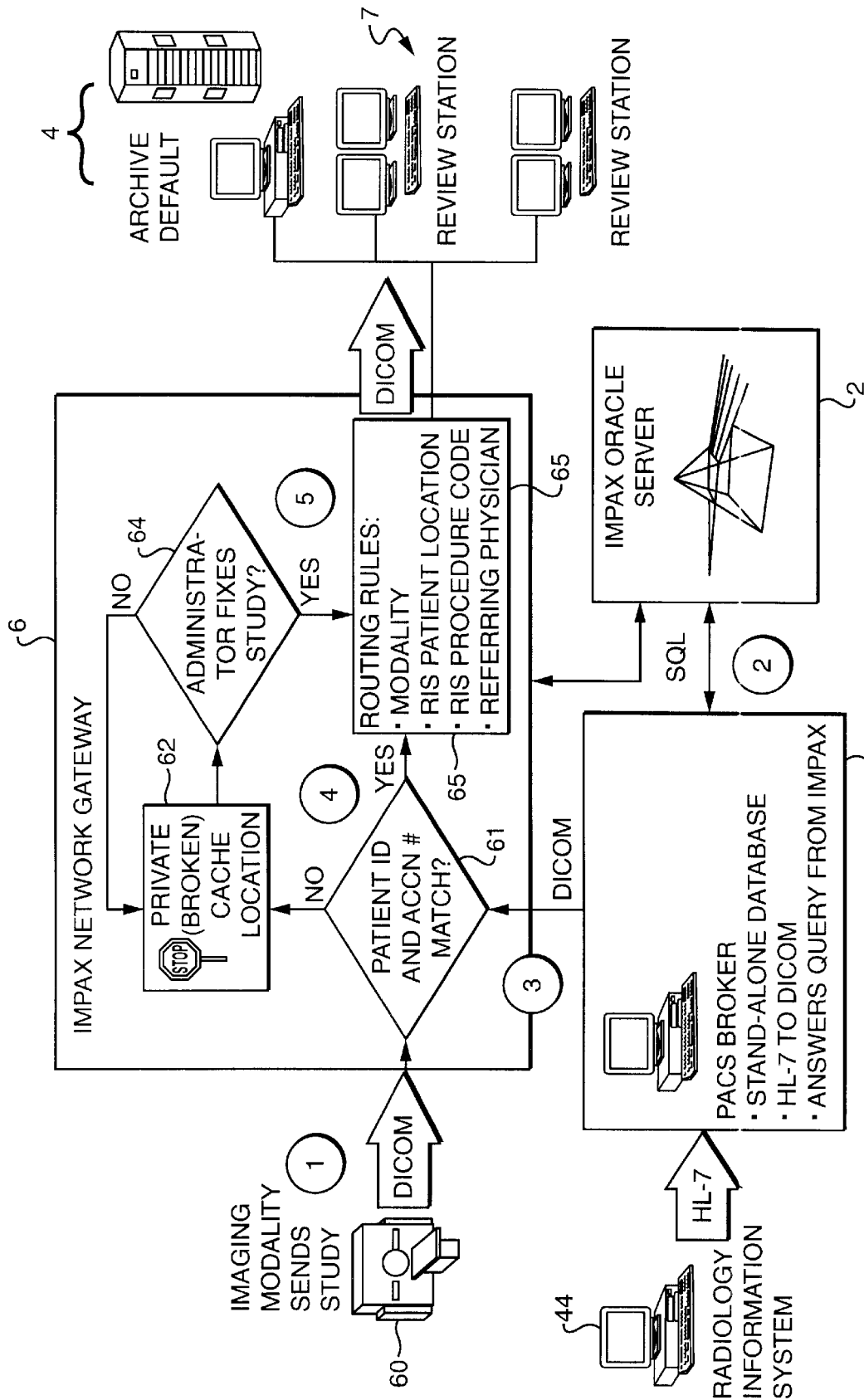
FIG. 4 shows routing of images by the PACS.

FIG. 4 shows the routing system of the present invention. More specifically, as shown, an imaging modality 60 or, alternatively, PACS broker 46, transmits a study to network gateway 6. Network gateway 6 then executes code to determine, in step 61, if the study is broken, meaning that it has demographic data that is incorrect in that is conflicts with information already contained on the PACS. In this regard, as noted above in section 1.3, the network gateway maintains study demographic information for validation purposes. This is the information used to determine whether a study is broken. In the event that the study is broken, the network gateway executes code in step 62 to store the study in its private cache, from which the PACS administrator may "fix" the broken study in step 64. Studies that are fixed, or that are not broken, are routed to appropriate PACS (e.g., reviewing) stations using routing rules, as shown in step 65. These routing rules may be created by the user, as described below.

Figure 5:
FIG. 5 shows a Web tool for creating routing patterns.

To this end, a service button in the PACS user interface (see section 3.1 below) displays a service menu "Web tool"

in response to clicking on a service action button. A representative example of the service menu "Web tool" is shown in FIG. 5. As shown, this service menu contains various "Installation" hyperlinks written in HTML which provide information regarding software used on the PACS (specifically, the Solaris® operating system, device EEPROM parameters, system variables, installation parameters, an installation log, and Solaris® and other software packages), and information regarding hardware used on the PACS (specifically, the system configuration, the system date and time, and tape drive information). Of interest with respect to routing, are the hyperlinks listed under "Configuration". These hyperlinks include DICOM network link 66, routing patterns link 67, referring physician link 69, patient location link 70, radiology specialty matching link 71, radiology specialties link 72, external specialty matching link 74, and external specialties link 75. In brief, these links allow a user to input information at the user's station, which information is then transmitted to the network gateway. The network gateway takes this information and generates (or updates) routing rules.

Starting with DICOM network link 66, this link connects to a site which displays a form which allows the user to set various PACS stations as potential recipients of routed studies. A representative example of this form is shown in FIG. 6. As shown, the form lists various PACS stations. In preferred embodiments of the invention, the user may input a "D" (for designation) next to a PACS station to indicate that the station is a destination (i.e., that it is a potential recipient), or a "T" (for transmit) next to a station to indicate that the station is a transmitting station. Obvious examples of destination and transmitting stations are reviewing stations and imaging modalities, respectively.

Figure 7:
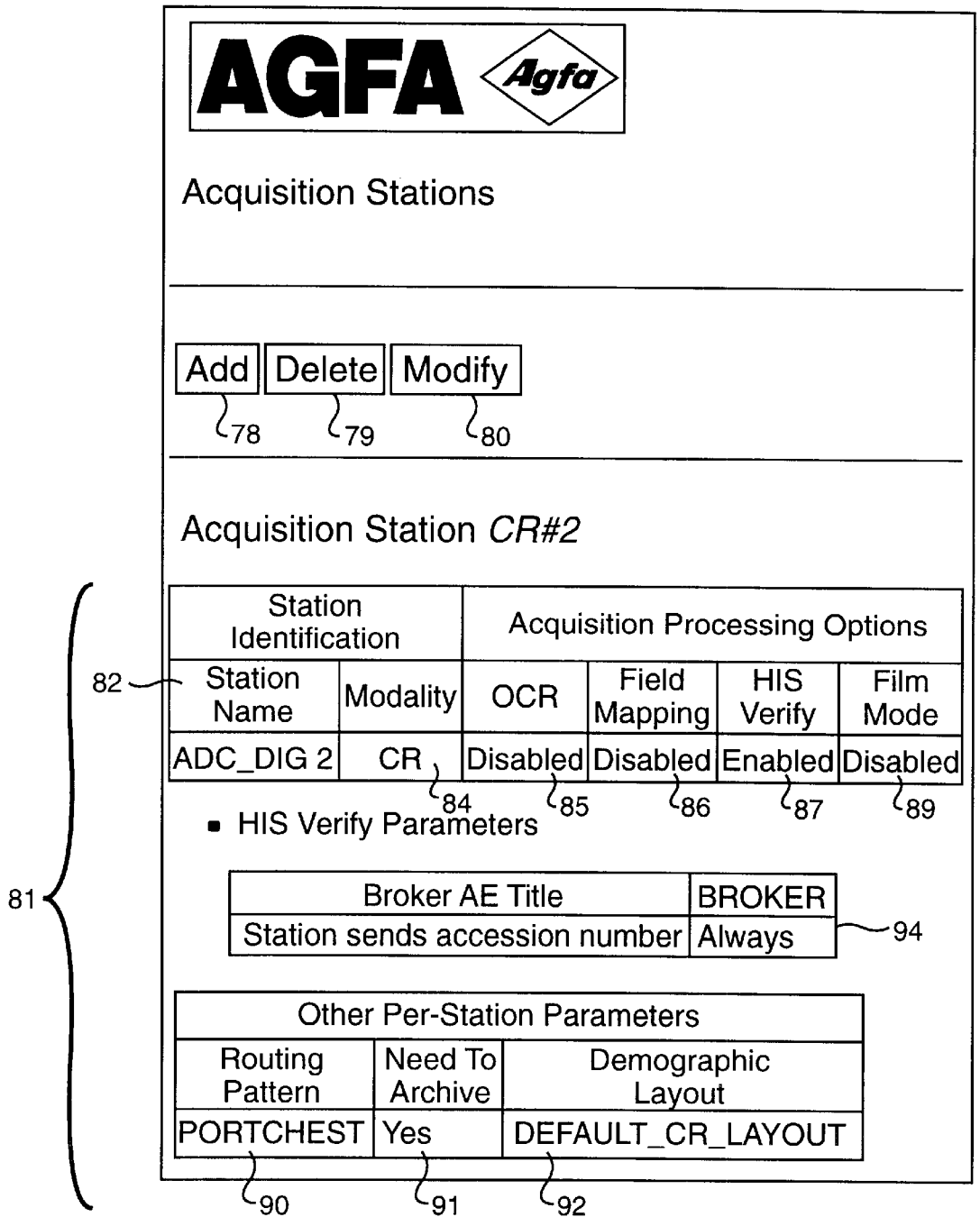
FIG. 7 shows a form which may be used to assign a routing name to imaging modalities in the PACS, and to provide other information regarding the imaging modalities to the PACS.

Acquisition stations link 76 connects to a site which displays a form which may be used to assign a routing name to each imaging modality, and to provide other information regarding the imaging modality to the PACS. An example of this form is shown in FIG. 7. The form includes add button 78, delete button 79, and modify button 80, together with table 81. Add button 78 is used to add the information in the form to the PACS, delete button 79 is used to delete the information in the form from the PACS, and modify button 80 is used to modify the entries in table 8 manually.

Table 81 includes station name box 82 for assigning an alias to the imaging modality (i.e., an acquisition station), modality box 84 for inputting the modality's type, OCR box 85 for selecting whether the station is a direct-capture device that outputs images requiring OCR, field mapping box 86 for inputting whether the modality requires DICOM mapping of an accession number or patient ID, HIS verify box 87 for setting the station as an HIS verified source, film mode box 89 for use with studies captured on film, routing pattern box 90 for inputting a routing pattern associated with the modality, need-to-archive box 91 for performing selective archiving of images output the imaging modality, demographic layout box 92 for creating names associated with demographic layouts provided for images produced by the modality, and accession number box 94 for entering an accession number associated with a study produced by the imaging modality.

Returning to FIG. 5, routing patterns link 67 displays a form on which a user may create routing rules and assign a set of attributes to each routing rule. The names of these routing rules may then be input to the acquisition station form described above. In more detail, clicking on link 67 connects to a site which displays the form shown in FIG. 8. This form includes add routing pattern button 95, delete routing pattern button 96, modify routing pattern button 97, and table 99. Add routing pattern button 95 adds the routing rule set forth in the table to the network gateway; delete routing pattern button 96 deletes the routing rule from the network gateway; and modify routing pattern button 97 allows the user to modify the routing rule.

Figure 10:
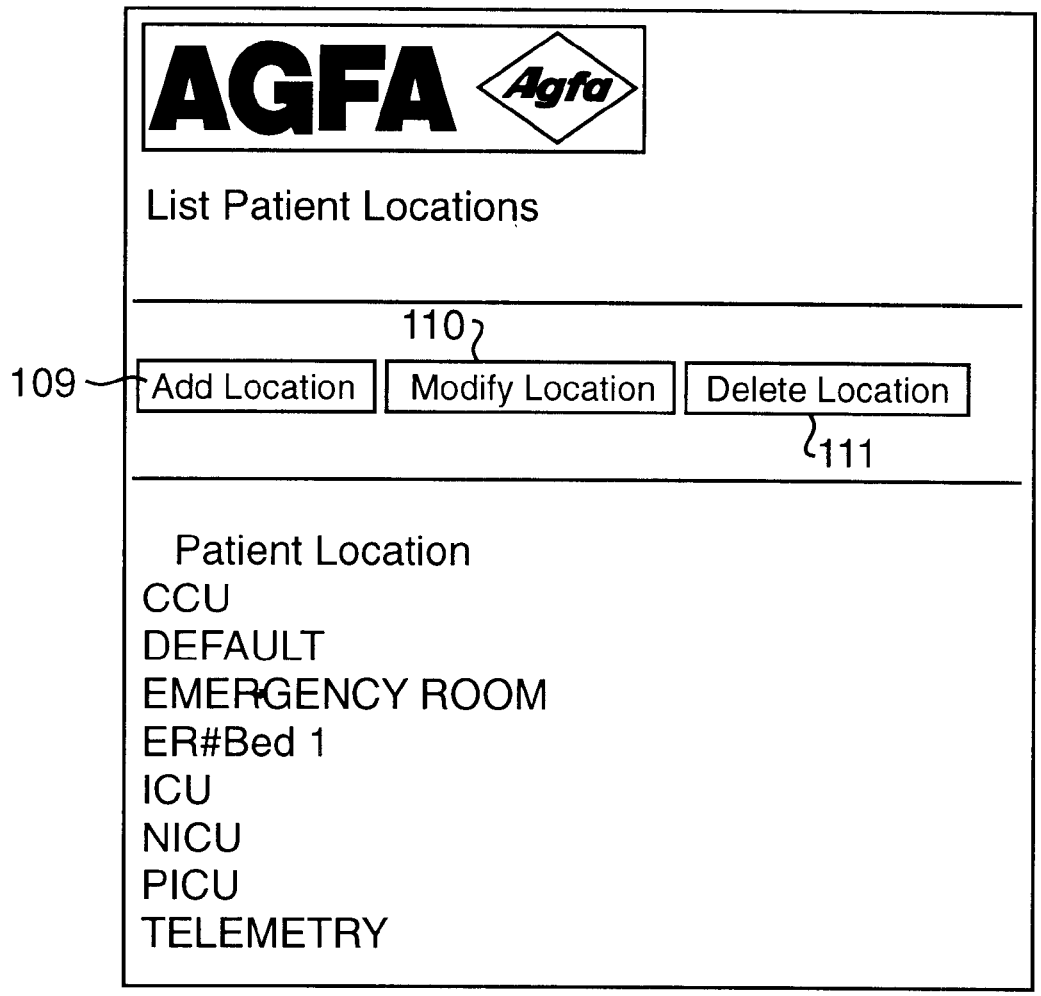
FIG. 10 shows a form which displays patient locations.

Table 99 includes name entry line 100 for assigning a name to the routing rule; destination entry line 101 for selecting a station to which studies will be routed by the rule; specialty entry line 102 for inputting a specialty (e.g., pediatrics, CR chest, CT abdomen, etc. or "Don't Care") which will invoke the routing rule; study status entry line 103 for inputting a minimum study status (e.g., new, dictated, preliminary, approved) which will invoke the routing rule; referring physician entry line 104 for inputting a referring physician to which the routing rule will apply; "apply routing to" entry line 105 for inputting a category of studies (e.g., "all" or "pre-fetched") to which the routing rule will apply; and "off peak schedule name" entry line 107 for selecting an off-peak time, such as weekdays, weekends or weeknights, during which the routing rule is to apply. Other entry lines which may be included in table 99 are a patient location entry line for routing based on patient location, and an arrival time entry line which is a variation of "off peak schedule name" entry line 107. FIG. 9 shows another example of a form for creating routing rules, which includes some, but not all, of the features described above Returning to FIG. 5, referring physician link 69 and patient location link 70 provide the user with separate libraries of potential referring physicians and patient locations for the PACS. For example, FIG. 10 shows a page which includes a list of potential patient locations, which can be accessed via patient location link 70. As shown in the figure, this page includes the abilities to add patient locations (add location button 109), to modify existing locations (modify location button 110), and to delete locations (delete locations button 111). A page which includes a list of potential referring physicians is substantially similar to that shown in FIG. 10, and is therefore omitted herein for the sake of brevity.

Radiology specialty matching link 71 and external specialty matching link 74 map RIS procedure codes to these specialties, thereby enabling organ-based routing (i.e., routing studies to reviewing stations based on bodily organs that the images therein depict). In this regard, each procedure performed on an organ is identified by an RIS procedure code. The present invention maps these RIS procedure codes to the above specialties. Then, when routing is performed based on a radiology specialty (e.g., MR, CT, etc.) or on an external specialty (e.g., pediatrics, emergency room, trauma centers, and orthopedics, etc.), organ-based routing is performed as well.

2.1 Pre-fetching

The present invention includes the ability to route relevant prior studies to a reviewing station in contemplation of a scheduled event, such as a patient examination or the like. This process is called pre-fetching, and is effected by code executing on the network gateway. In more detail, pre-fetching involves RIS gateway 46 receiving information concerning a scheduled event from RIS 44, and then transmitting that information to the PACS, in particular to network gateway 6 (see FIG. 1). The network gateway then queries the RIS, via the RIS gateway, requesting details concerning the scheduled event. For example, the network gateway can request information concerning the nature of the scheduled event (e.g., an exam, consultation, surgery, etc.), the time and date of the scheduled event, and the body part pertaining to the scheduled event, among other things.

Once the network gateway receives the requested information from the RIS, predetermined PACS pre-fetching rules stored in memory on the network gateway take over to retrieve relevant prior studies from a memory (e.g., the archive) on the PACS. These pre-fetching rules may be set/modified by the user via relevant prior rules link 112 on the form shown in FIG. 5, as described below. Initially, the pre-fetching rules are used to determine which prior studies on the PACS should be retrieved. Once this is done, the prior studies are copied into the archive station's cache (or, alternatively, the network gateway's cache) and routed to the appropriate stations automatically. In cases where a recipient station is cache-less (e.g., a cache-less reviewing station), the network gateway will merely copy the relevant prior studies to cache without routing them automatically. That is, in this case, the network gateway waits for a request from a PACS station before routing retrieved images thereto. Of course, the behavior of the network gateway is dictated by the applicable pre-fetching rules (together with the details received from the RIS).

In this regard, as noted above, the pre-fetching rules may be set and/or modified by the user via relevant prior rules link 112. More specifically, clicking on relevant prior rules link 112 connects the user to a site which contains a form used for inputting information to add, delete and/or modify pre-fetching rules. Once this information is input into the form, the information is conveyed back to network gateway 6, which generates pre-fetching rules therefrom, stores these rules in memory, and executes them as required. An example of this form is shown in FIG. 11. This form includes add button 114 for adding the pre-fetching rule defined by table 115, delete button 116 for deleting the pre-fetching rule, and modify button 117 for modifying the pre-fetching rule. Representative pre-fetching rules are shown in FIG. 11, and are set forth below in Table 4.

TABLE 4

Pre-fetching Rules

| Rule | Available Choices | What it Does |
| --- | --- | --- |
| Radiology Specialty | All internal and external specialties | Allows the user to selectively configure pre-fetching of images relating to particular specialties. |
| Modality | All modalities in the PACS | Allows the user to selectively configure pre-fetching of images generated from particular imaging modalities. |
| Fetch Same Specialty | Yes/No | Looks at the speciality of a new study and does or does not, pre-fetch prior studies comprising the same specialty. |
| Fetch Same Modality | Yes/No | Looks at the modality that created a new study and does, or does not, pre-fetch prior studies created by that modality. |
| Maximum Number of Studies | Enter Whole Number | Indicates the maximum number of studies that can be pre-fetched. |
| Oldest Study to Fetch | Enter Whole Number In Years | Indicates that only studies captured after a predetermined date will be pre-fetched. |
| Fetch Summary | Yes/No | Fetches relevant prior studies' summaries along with the studies themselves (if present). |
| Fetch Only Summary | Yes/No | Fetches relevant prior studies' summaries, but not the studies themselves. |
| Route Priors | Yes/No | Indicates whether, after the studies have been copied to archive cache, they are to follow the routing rules configured above. |

TABLE 4-continued

Pre-fetching Rules

| Rule | Available Choices | What it Does |
| --- | --- | --- |
| Cache Priors | Yes/No | Indicates whether retrieved studies are to remain in the archive's cache, from which they can be retrieved. |

Of course, it should be noted that the invention is not limited to the pre-fetching rules shown above, and that any others may be incorporated herein. Moreover, the foregoing pre-fetching rules can be combined, where appropriate, as desired.

3.0 User Interface

The main study window (alternately, the study management window) is the primary user interface for each of the above-described PACS stations (both core components and extensions, where appropriate). The main study window is implemented and controlled by PACS software modules running on each PACS station. As shown in FIG. 12, the main study window includes a main study list 116, system status indicators 117, and two sets of action buttons 118 and 119. Action buttons 119 enable a user to view, retrieve, transmit, and delete studies. These buttons also allow a user to perform administrative functions and exit the system. Action buttons 118 allow a user to sort patient studies by modality, creation time, patient name, and other criteria. These buttons also permit users to select, restore and save worklists. Which of action buttons 118 and 119 are available in the main study window depends, at least in part, upon settings in the user's profile, as described in more detail below. The PACS administrator, however, can limit the action buttons available to particular users and to particular stations, regardless of the settings in that users's profile.

Status indicators 117 provide information about the PACS. In brief, left-most segment 120 displays an amount of available local memory. Its color changes from green to amber to red as the local memory fills. Second segment 121 displays system activity levels during a retrieve operation. The retrieve queue of the station can be viewed by pointing and clicking to this segment. Third segment 122 displays system activity levels during study transmission. Fourth segment 123 indicates that there are pending off-line jobs for MODs not physically present in the jukebox. This segment is usually provided on archive stations only; although this is not a requirement. Fifth segment 124 indicates if there are any "broken" studies in the station's private cache. This segment is usually provided on the network gateway and the archive stations only; although this is also not a requirement.

3.1 Action Buttons

When the user clicks on an action button in the main study window, the PACS (specifically, the PACS software on the station) carries out an action, usually with respect to a selected study or studies. The following is a description of the various action buttons that may be provided in the main study window, and the processes associated therewith.

Display button 125 enables a user to display one or more selected studies in the main study list simply by clicking on the button. Specifically, in response to a user clicking on this button, the PACS software retrieves selected studies from the station's cache, and then displays the selected studies on the station's display screen. Display button 125 also initiates "pipeline" retrieval of images described below in section 6.0. In preferred embodiments of the invention, display button 125 is found on reviewing stations only. However, other embodiments of the invention also provide it on one or more of the archive station, the database server, and the network gateway, as well.

Retrieve button 126 enables a user to retrieve one or more selected studies. More specifically, in response to a user clicking on this button, the PACS retrieves selected studies into the user station's cache, usually prior to display. In this case, the PACS software usually retrieves studies from the archive station.

Transmit button 127 enables a user to transmit one or more selected studies from local cache on the user's station to another PACS station. To this end, in response to a user clicking on button 127, the PACS software displays a dialog box (not shown), in which the user may specify the location of a receiving PACS station or the like, as well as other relevant parameters. As noted above, the PACS puts limitations on where studies, particularly edited studies, can be stored. These limitations generally cannot be circumvented via transmit button 127.

Merge button 129 merges two or more selected studies with matching patient IDs, accession numbers, and/or study IDs into one study folder. Thereafter, the study folder is treated by the PACS as a single study, meaning that it is transmitted, routed and received as if it were a single study. In order to merge studies-, they should remain in a station's cache, and off the archive's jukebox. In preferred embodiments of the invention, the merge button is provided on the archive station and the network gateway only; however, other embodiments may include it on all or some of the other stations.

Split button 130 splits a folder of studies. Splitting is a process whereby images are removed from one study and pasted into the folder of another study. It is most often used to split folders which include studies that have been unintentionally combined (e.g., studies of different patients). This can occur in some imaging modalities where the technician fails to close an exam before starting another. A folder should be stored in a station's cache, and off the jukebox, before it is split. In preferred embodiments of the invention, the split button is provided on the archive station and the network gateway only; however, other embodiments may include it on all or some of the other stations.

Delete button 131 deletes one or more selected studies from a station's cache. This button is preferably provided on all PACS stations; however, it is most often used on the reviewing stations to delete studies that have been reviewed. In the event that a selected study is the only copy of that study on the entire PACS, the PACS software will issue a warning indicating that the user is deleting the last copy of that study on the system and will request confirmation before the study is actually deleted.

Print button 132 prints a selected study, series of images, or individual image based on printer settings for the station. The copy of the study in the station's cache is the copy that is typically printed; although the invention can be configured to retrieve a "new" copy of the study from the archive or elsewhere and print that new copy. Preferred embodiments of the invention also provide a user with printer options, provided that there is more than one printer connected to the PACS. Examples of printers that are compatible with the PACS are provided in section 1.6.7 above.

As noted above, certain studies may be protected from auto-deletion by assigning them a protected (or "P") status. Protect button 134 effects this operation on one or more selected studies. Studies may be protected on any of the PACS stations described above. An indication that a study is protected is provided in the main study list and worklist, as described in more detail below in section 3.2.

Show Report button 135 permits a user to retrieve, and to display on his station, a patient report from the HIS or RIS. As described above, in order to obtain information from the HIS or RIS, a PACS broker (i.e., RIS gateway 46) is typically required on the PACS. Accordingly, the show report button is generally only included in PACS that include a PACS broker. Of course, the show report button may also be used in cases where the PACS is connected to the HIS/RIS via means other than a PACS broker.

Study information button 136 displays a form relating to one or more selected studies. This form includes information about the studies and/or about the patient associated with the studies. In preferred embodiments of the invention, the user is able to set, in advance, the format of the form and the patient and/or study information that is to be included in the form.

FIG. 13 shows a representative example of the study information form displayed by button 136. As shown, study information form 137 includes entries for patient ID, name, sex, location, study ID, date, time, station, accession number, procedure, modality, physician, reported status, study status, specialty, private field, comments, reason, and keywords (user-assigned word(s) for identifying a study quickly from a list of studies). Also included in the form are action buttons. In this regard, button 139 saves comments and changes to the patient study information; button 140 closes the study information window; and button 141 performs RIS validation, meaning that it inserts the actual patient ID and accession number into the study. In this regard, in trauma cases in particular, a study may be forced into the PACS without going through RIS validation. When this is done, the invention inserts a UID (i.e., "unidentified") string for the patient ID. Button 141 thus substitutes the patient's ID for the UID string.

Returning to FIG. 12, process monitor button 143 enables a user to monitor and to change the status of archive, gateway, print and transmit jobs stored in PACS stations caches. In brief, as noted above, and as described below in section 3.2, each study in the main study list and worklist has a status associated therewith. In response to a user clicking on process monitor button 143, the PACS software displays a form containing the status of one or more selected studies, preferably, on any of the stations in the PACS. This form can then be edited to alter jobs' status or the like. The process monitor is described in greater detail below in section 4.2.1.

An archive administration button, shown in FIG. 14, can also be included in the main study window. The archive administration button permits a user to prepare, import and export MODs for the archive station's jukebox. In preferred embodiments of the invention, this button is provided only in the main study window of the archive station; although this is not a requirement. FIG. 14 also shows a form that the PACS software displays in response to a user clicking on button 144. This form include two rows of action buttons. The top row of action buttons is always active, while the bottom row of action buttons becomes active only after an archive process has been halted.

With respect to the top row of action buttons in form 145, this row contains button 146 which interrupts all archiving activity. That is, after this button is activated, stored and retrieved jobs will continue to enter the appropriate queues, but will not be acted upon until the archive process is up and running again. Button 147 re-starts the archive process so that all pending retrieved and stored jobs can be processed; button 148 allows a user, after selecting one optical disk from volume list 149, to view a form (not shown) that lists the study ID, study date, and number of pages of selected studies on a disk; button 150 refreshes the form shown in FIG. 14; and button 151 exits the archive process.

With respect to the bottom row of buttons in form 145, button 152 starts a recovery process whereby the station checks all of the disk locations inside the jukebox; button 154 imports a new optical disk into the jukebox and assigns it a volume ID; button 155 moves a disk to an import/export element at the top of the jukebox; button 156 erases the contents of any optical disk that is not hard-wired protected; button 157 formats a fresh optical disk so that it can be imported; button 159 performs a quick check of the jukebox disks to ensure that each is inserted in its correct slot; and button 160 ejects disks from the drives and returns them to their appropriate mail slots. Status indicators in form 45 indicate whether a disk is Fresh, meaning that it has not yet been written to; Open, meaning that it has room for more studies; Closed, meaning that it is filled; Protected, meaning that it may not be erased; or Foreign, meaning that it was created on a different PACS archive.

Returning to FIG. 12, as noted above, the invention provides a way to customize the main study window and display tool bar based on information input to a user profile form and/or an access control form. Users button 161 displays these forms, shown in FIGS. 31 and 30, respectively. Section 5.0 below describes, in detail, customizing the main study window and tool bar using these forms.

A backup button (not shown) may also be provided in the main study window to initiate backup of the PACS database. This usually means storing the PACS database to DLT or, alternatively, MOD. In preferred embodiments of the invention, this button is provided on the database server station only; however, other embodiments of the invention provide it on other stations as well.

Fix study button 162 calls up a "fixup" GUI which enables a user to modify or to alter information relating to broken studies. As noted above, a broken study is a study with demographic data that is incorrect or that conflicts with information already contained on the PACS. A broken study can be detected in the main study window based on an indicator (not shown) appearing to the right thereof. Such studies typically remain in the network gateway and are not available to reviewing stations; hence button 162 is usually provided only on the network gateway.

Figure 15:
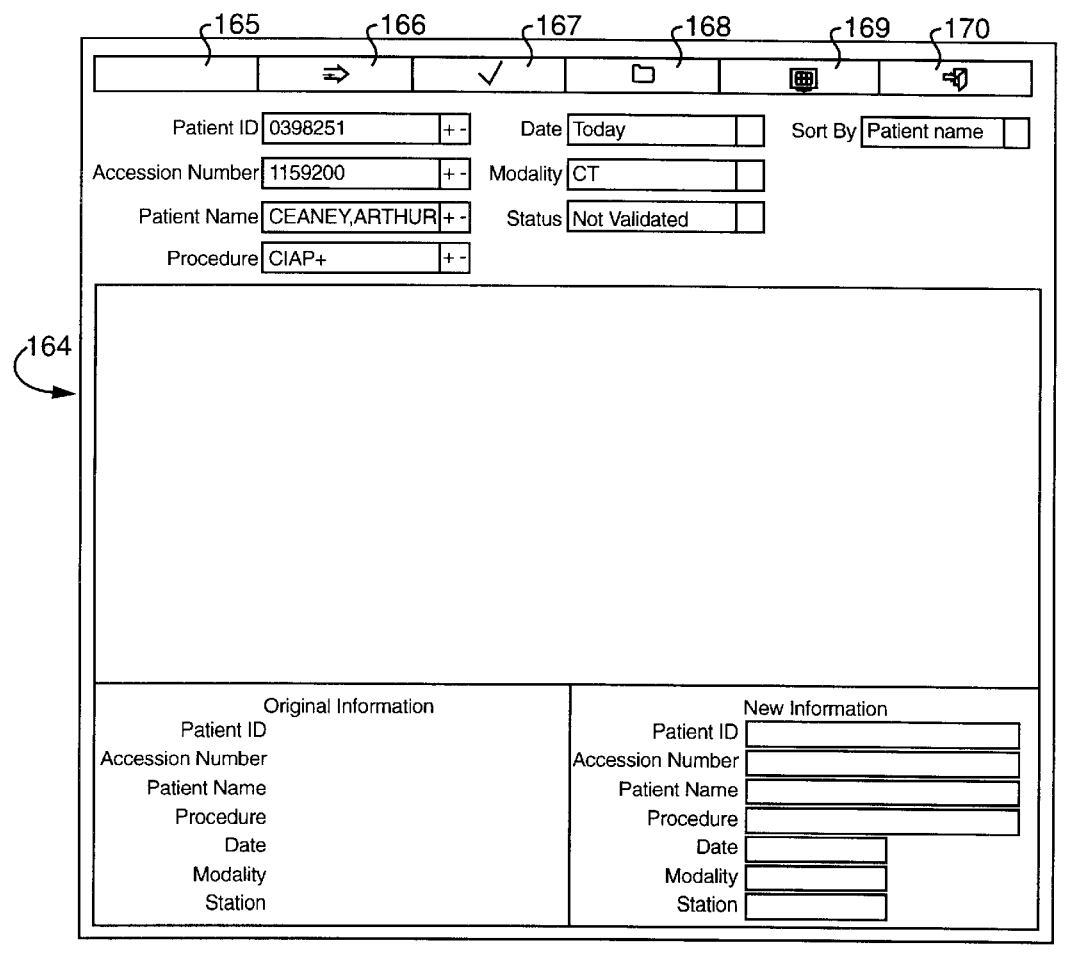

In response to a user clicking on button 162, the PACS software displays fixup GUI 164, shown in FIG. 15. GUI 164 displays the information pertaining to the broken study, and allows the user to correct incorrect information. To this end, the fixup GUI 164 includes action buttons, which buttons include button 165 for clearing the original study information, button 166 for restoring cleared study information, button 167 for testing newly-input study information to determine whether the study has been "fixed", button 168 for forcing the study into the public cache once it is determined that the study has been fixed, button 169 for viewing the study, and button 170 for closing the GUI. A similar form may also be provided on the RIS gateway to fix broken studies received from the RIS.

HIS window button 171 permits a user to open a "telnet" session between the PACS and the HIS/RIS via the PACS broker, database server, and network gateway. During this telnet session, the user may view requested patient information and RIS events, preferably in real-time. This button is typically provided on the reviewing stations, but may be available on other PACS stations as well.

Service/configure button 172 is used by the PACS administrator to set up the PACS and all network gateway functions, including the routing and pre-fetching rules described above in section 2. The service button is also used to check the capacity of caches in the various PACS stations using installed service tools.

Sign off button 174 closes the PACS application and places the user at a login screen. The user may re-enter the PACS by entering both a user login ID and a password.

Custom query button 175 enables a user to query for patient images, studies and/or folders on the PACS. When activated, the custom query button displays a form, which the user may fill out in order to specify attributes of images, studies and/or folders stored on the PACS that the user wants to retrieve. FIG. 16 depicts the form displayed by clicking on custom query button 175. On this form, the user may enter a range of search dates, times, patient information, RIS procedure codes, or other relevant information on which to base the custom query. Similarly, the user may initiate location sorting by activating location sorting button 178; status sorting by activating status sorting button 177, and modality sorting by activating modality sorting button 176. The sorting effected by these buttons is substantially identical to that described below. Once the relevant information has been set in custom query form, searching may be initiated by clicking on search button 179. Thereafter, images, studies and/or folders which match the search criteria are retrieved and displayed in the study list. Clear search criteria button 180 is also provided in the custom query form to clear existing entries, and exits close button 181 from the custom searching function.

Returning to FIG. 12, default query button 182 applies default sort and select criteria for the user based on the user's login ID. This default criteria may be specified, and subsequently changed, by altering the user's profile. This may be done at login, or at any point during execution of the PACS.

Worklist select button 184 selects studies that match default worklist criteria set forth in the user's profile. For example, this button may be configured, via the user profile, to select all CT NEURO (i.e., computed tomography neurological) studies from the main study list. The button may be configured to select relevant prior studies as well, as described below.

Save worklist button 185 permits a user to save selected studies as a worklist. This save operation saves the worklist over station power cycles and user logouts. Restore saved worklist button 186 restores a worklist that was saved previously.

Location sorting button 187 permits a user to display a list of all studies residing at a particular location in the PACS. Clicking on location sorting button displays a pull-down menu which includes a list of optional searching locations. These locations include "Local" (which is shown), which displays a list comprised only of studies contained on the station's local storage (e.g., its cache); "System", which displays a list comprised only of studies on the PACS; and "Cached", which display a list comprised only of studies that reside on caches within stations in the PACS cluster. An "Other targets" option may also be displayed, by which a user may display a list comprised only of studies at user-specified locations in the PACS. These locations may be specified, e.g., in the access control form described below.

Time sorting button 189 permits a user to select and to list studies in the main study list based in their creation date and/or time. More specifically, clicking on time sorting button 189 displays a pull-down menu which includes time-oriented options for sorting through studies in the study list. These options include "Any time" (which is shown), which selects and lists all studies in the main study window regardless of when they were created; "Today", which selects and lists only studies which were created today; "Yesterday", which selects and lists only studies which were created yesterday; and "Last 2, 7, 21", which selects and lists only studies which were created within the specified time period, i.e., 2 days, 7 days, 21 days, etc. In preferred embodiments, the PACS software provides the option of creating a customized "prior days" query by altering parameters in the user profile form.

Parameter sorting button 190 enables a user to select and to list studies in the main study list based one or more input parameters. Specifically, clicking on parameter sorting button 190 displays a pull-down menu which includes the following sorting options: "patient name", "patient ID", "accession number", "patient location", "radiology specialty", "referring physician", "private field" (i.e., a user-specified field), and "unspecified" (no sorting—this is shown). The user may then select one of the foregoing options for searching through the study list. Once an option has been selected, the user specifies an entry in box 191 which corresponds to the specified field. For example, if the "accession number" option is selected from the pull-down menu, the user may enter an accession number into box 191. "Wild cards" can be entered into box 191 to enhance functionality. The PACS software then searches for the specified study or studies, and selects and lists only those studies in the main study window.

List ordering button 192 permits a user to reorder a list of studies in the main study list based on parameters provided in a pull-down menu. Specifically, clicking on list ordering button 192 displays a pull-down menu which includes the following options: "Recent last", "Recent first" (which is shown), and "Name". "Recent last" reorders the study list in chronological order. "Recent last" reorders the study list in reverse chronological order. "Name" reorders the study list alphabetically by name. Other options, of course, may be provided as well.

Modality sorting button 194 permits a user to select and to list studies in the main study list based on the imaging modality used to generate images in the studies. More specifically, clicking on modality sorting button 194 displays a pull-down menu which includes modality-oriented options for sorting through studies in the study list. These options include "CT", which selects and lists only studies produced by a CT imaging modality and which is shown; "MR", which selects and lists only studies produced by an MRI imaging modality; "US", which selects and lists only studies produced by a US imaging modality; "CR", which selects and lists only studies produced by a CR imaging modality; "NM", which selects and lists only studies produced by an NM imaging modality; and "Any", which provides no modality sorting. Additional modalities can be added to the pull-down menu by changing parameters in the access control form, as described below.

Status sorting button 195 permits a user to select and to list studies in the main study list based on the status of the study. More specifically, as noted above, each study may have a status associated therewith. Up to this point, the only status described has been protected, or "P". However, there are numerous additional status designations that may be associated with each study. At this juncture, suffice it to say that there are at least five additional status designations: new ("N"), dictated ("D"), in the process of being dictated ("d"), reported ("r"), and approved ("R"). Definitions of these (and other) status designations are provided in section 3.2 below. Clicking on status sorting button 195 displays a pull-down menu which includes status-oriented options for sorting through studies in the study list. These options include "new", which selects and lists only new studies; "dictated", which selects and lists only dictated studies or studies in the process of being dictated; "reported", which selects and lists only reported studies; "approved", which selects and lists only approved studies; and "any" (shown), which does not perform status sorting, meaning that all studies remain listed regardless of their status. Of course, this selection list can be modified to select and list studies based on other status designations.

Display listing button 196 enables a user to customize the format of the study list. Clicking on display listing button 196 displays a pull-down menu which includes a list of display options. These options include "Study", which displays a list of studies; "Study & Summary", which displays a list of studies and summaries associated with those studies; "Patient & Study", which provides a listing of all studies for each patient, where the patient name is listed only once and all studies are listed line-by-line; and "Patient", which displays studies for a particular patient only.

Basic query button 197 initiates searching, sorting and reordering based on criteria set in the pull-down menus of location sorting button 187, time sorting button 189, parameter sorting button 190, list ordering button 192, modality sorting button 194, status sorting button 195, and display listing button 196. That is, after the appropriate criteria are specified via the pull-down menus, the selected criteria are displayed on the main study list. For example, as shown in FIG. 12, modality sorting button 194 is configured to select and list studies from CT imaging modalities. A user then initiates the actual searching/sorting/listing by clicking on basic query button 197. Until this is done, the main study list will not be altered regardless of what has been set via the pull-down menus.

Various options are available in connection with basic query button 197. For example, it is possible to cancel a search midway through by double-clicking on basic query button 197. In addition, it is possible to set and to leave the basic query button in the active position. Doing this effectively results in automatic searching/sorting/listing whenever new criteria are set in the pull-down menus.

Although not shown in FIG. 12, additional action buttons may also be displayed in the main study window. These additional buttons include a "Copy to Cache" button which copies studies from jukebox MODs to the local hard disk on the archive station; a "Copy to Jukebox" button which copies selected studies from local hard disk or RAID to the jukebox; and a "Configure" button which sets up the PACS network and network gateway functions, sets data staging rules, and checks station cache. The former two buttons are typically provided only on the archive station; although this is not required by the invention.

3.2 Study List

Study list 116 contains folders with studies, images and image-related information. Each line in the study list contains information about one study or one patient. Name and column headings are managed through system-wide controls in the access control form. In preferred embodiments of the invention, there are up to 16 fields in the study list. These fields are set forth below in Table 5.

TABLE 5

Study List Fields

| Field | Definition |
|---|---|
| Accession Number ("#") | The unique ID or job number that is generated by the RIS and that is used to track each exam (i.e., study), and its corresponding patient name, date, and exam type. |
| Patient ID | The patient's identification number. |
| Patient Name | The patient's name, last name followed by first name, with the fields separated by commas. |
| Modality | A two-letter code for the type of imaging modality that acquired the study (e.g., MR, CT, US). |
| Study ID | A unique identifier that a modality creates for each study. |
| Study Date | The month, day and year that the study was created. |
| Study Time | The hour, minute and second that the study was created. |
| Procedure | The RIS examination code. This code specifies the nature of the examination (i.e., the study description). |
| Station | The station name of the acquiring imaging modality. |
| # of Images | The number of images for each study or patient. |
| # of Studies | The number of studies associated with each patient name. |
| Status | The status of each study on the local hard disk (cache). |
| Patient Location | The RIS patient location field (if present in DICOM). |
| Radiology Specialty | The body part that has been mapped to the RIS exam code. |
| Physician | The name of the referring physician (if present in DICOM). |
| Private Field | May be configured by the user to display another DICOM field. |

As noted above, the PACS study list provides information about each study folder in the form of status designations. In cases where the PACS is networked to a RIS that broadcasts changes in study status, the PACS software will automatically update the status designations. Otherwise, the status designations may be changed manually. Each study folder will have one or more of the status designations set forth below in Table 6.

TABLE 6

Status Designations

| Status | Definition |
|---|---|
| "C" | Cached status, meaning that the study resides on a station hard disk/RAID somewhere in the PACS cluster. |
| "D" | Dictated status, meaning that a radiologist has viewed the study and dictated a preliminary report. |
| "d" | Indicates dictation of a preliminary report is in progress. |
| "H" | Hard copy status, meaning that a printout has been made of the study. This status indicator preferably remains with the study always. |
| "I" | Indicates additional study comments in a study "Info" form. |
| "L" | Local status, meaning the study is contained in memory on the local hard disk. In preferred embodiments of the invention, only local studies may be viewed, printed and transmitted. |
| "l" | Indicates that the study is in the process of being transmitted to this destination. This changes to an "L" once the study is received. Studies with an "l" status may be viewed via the pipelining process described below. |

TABLE 6-continued

Status Designations

| Status | Definition |
|---|---|
| "M" | Indicates that the study has been archived to a MOD. |
| "m" | Indicates that only part of a study has been archived. This generally means that there are configuration problems with the PACS routing rules or that there is a problem with the archive. |
| "N" | Indicates that the folder is new to the PACS. |
| "O" | Indicates an offline status, meaning that the study resides in an archive disk that is not present in the jukebox. |
| "P" | Protected status, meaning that the study will not be deleted automatically. |
| "r" | Reported status, meaning that a report was created in the HIS/RIS. |
| "R" | Indicates that a report on the study has been approved. |
| "T" | Indicates that the study resides on DLT. |
| "V" | Indicates that the study has not yet been viewed. |

4.0 Image Display

Figure 17:
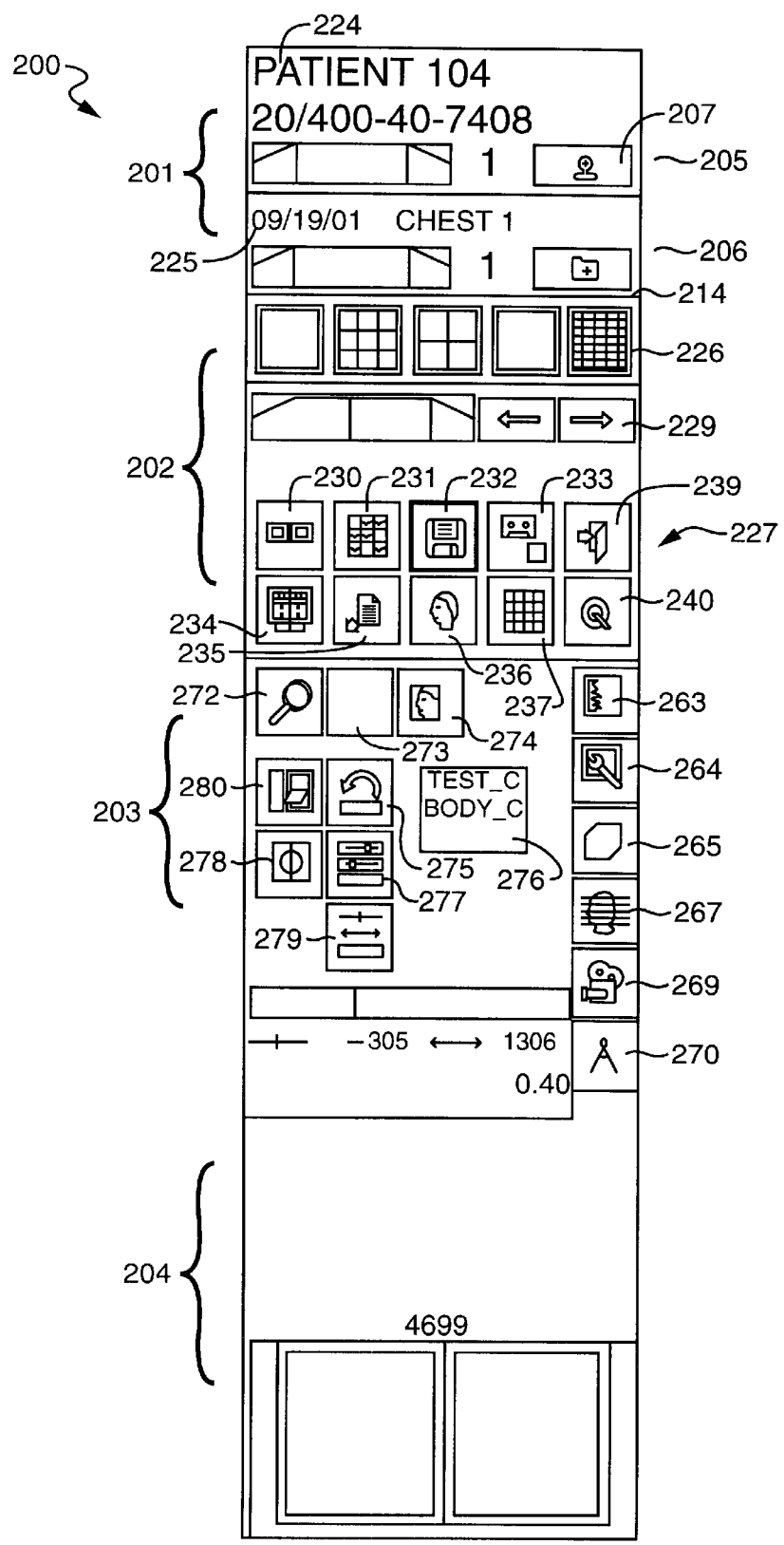
FIG. 17 shows a toolbar used in PACS displays.

Once images have been selected from the main study list, the images may be displayed on a PACS station. Accompanying the display of such images is a toolbar which enables a user to edit, manipulate, and view the images. This toolbar is implemented and controlled by PACS software modules running on each PACS station. FIG. 17 shows an example of such a toolbar. As shown, toolbar 200 is divided into four major sections that allow the user to view and to act on images. The four major sections of the toolbar comprise worklist section 201, format selection section 202, image manipulation section 203, and virtual screen 204.

4.1 Worklist Section

Figure 18:
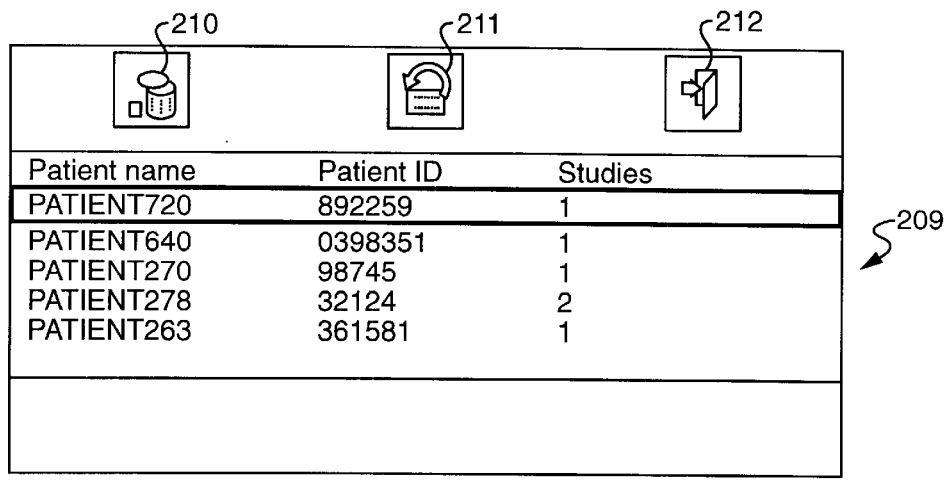
FIG. 18 shows a form that displays patient information.

The worklist section of toolbar 200 is divided into two parts 205 and 206 that contain sliders for scrolling through the worklist and for selecting the studies listed for individual patients. The slider in part 205 is active if there are different studies having associated therewith two or more patient names. The first part of worklist section 201 also contains action button 207. This button displays the window shown in FIG. 18. As shown, window 209 includes button 210 for deleting a study from the worklist, button 211 for restoring a saved worklist, and button 212 for closing the patient worklist.

Figure 19:
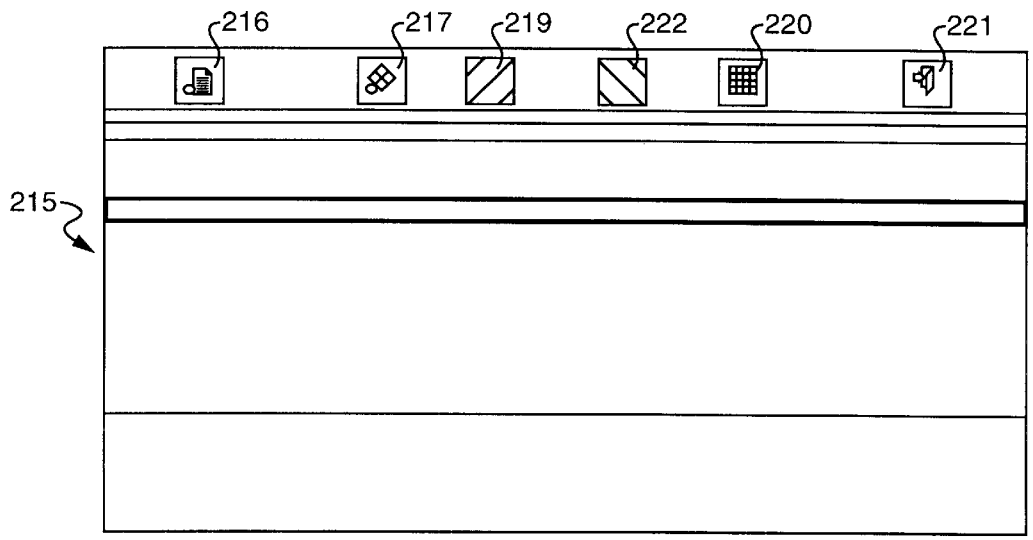
FIG. 19 shows a form that displays study information.
Figure 20:
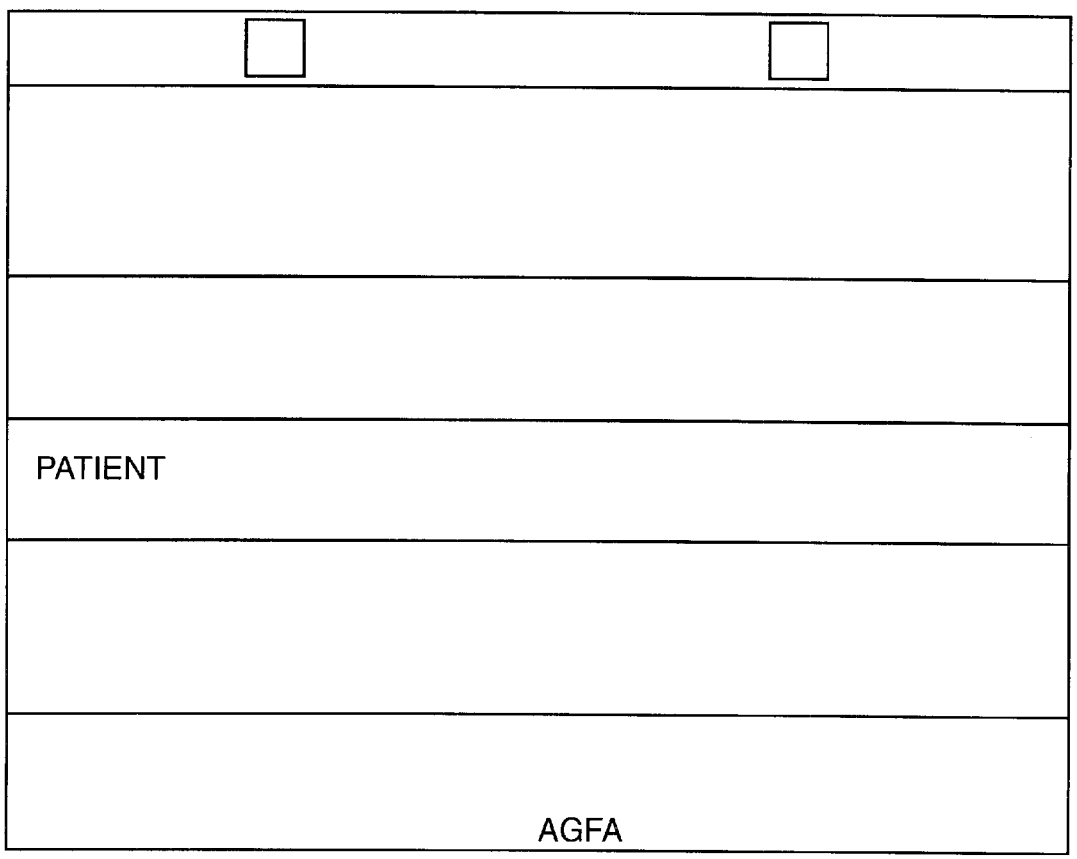
FIG. 20 shows a form that displays additional study information.

The second part of worklist section 201 also includes a slider for scrolling through the worklist. This slider is active if there is more than one study in the worklist. Also included in this part of the worklist section is action button 214 for accessing information about all studies associated with a specific patient. Specifically, when activated, button 214 displays the window shown in FIG. 19. As shown, window 215 includes button 216 for requesting an HIS/RIS report for a highlighted study, button 217 for retrieving a study and its corresponding summary, button 219 for removing a study from the worklist, button 220 for listing summaries associated with studies, button 221 for closing the study worklist, and button 222 for transmitting a locally-stored study to a selected destination. In this regard, upon activating button 222, a form (not shown) is displayed, from which the user may select or, alternatively, input one or more destinations to which the selected study is to be transmitted. Section 201 also includes patient and study identifiers 224 and 225, respectively, as also shown. Clicking on either of these fields displays a form, shown in FIG. 20, which provides additional information about a study. Comments regarding the study may be input to this form and thereafter saved.

4.2 Format Section

Format section 202 of the toolbar contains buttons 226 for selecting a display format for patient images. Additional action buttons 227 in this section enable display annotation, comparison, marking of a study for dictation, creating a summary series, displaying HIS/RIS reports, and exiting the display. In addition, tab buttons 229 enable a user to tab through displayed images based on pre-set image tabs. In this regard, the present invention provides a way to set tab stops in displayed images. Specifically, the invention permits a user to point and click on displayed images at points where tab stops are to be set. When instructed, e.g., by clicking on a "save" action button, the invention stores these tab settings in its local cache, together with the displayed images (as noted, displayed images are typically displayed from a reviewing station's local cache). These tab setting can later be modified or deleted simply by calling-up a form on which they are stored.

Included within action buttons 227 is study display format button 230 which toggles between different study display formats. In the present invention, there are preferably three options: one study per monitor, one study spans two monitors, and on study spans four monitors. The action button displayed indicates that one study spans two monitors (hence the use of two "monitors" on the button). Clicking on that button causes the display format to change, hence the use of "toggle". Action button 231 enables a user to select images within an exam and to save them as a separate series of images. Action button 232 enables a user to save changes in the display. Action button 233 enables a user to mark studies for dictation. This button toggles between three states, preferably: "off", in which the study has a "new" status and is therefore ready for dictation (this is shown); "dictation in process" which indicates that the study is currently being dictated; and "dictation complete" which indicates that dictation for the study has been completed. Action button 234 enables a user to display one series of images on a left monitor (e.g., the left half of a display screen) and another series on the right monitor (e.g., the right half of a display screen), The button toggles between the "AA" position (as shown), where the same series spans two viewing monitors, and the "AB" position (not shown), where different series span the two viewing monitors. Action button 235 allows the user to display a report form for a current study. Action button 236 allows the user to display an annotation for a displayed image. Action button 237 allows a user to set whether toolbar inputs are to affect only a single image or all images in a series or study of images. Action button 239 allows a user to exit from the display mode and return to the main study list. Finally, action button 240 comprises the process monitor, which allows the user to open a form wherein the user can check the status of transmit, receive, and print jobs.

4.2.1 Process Monitor

Figure 21:
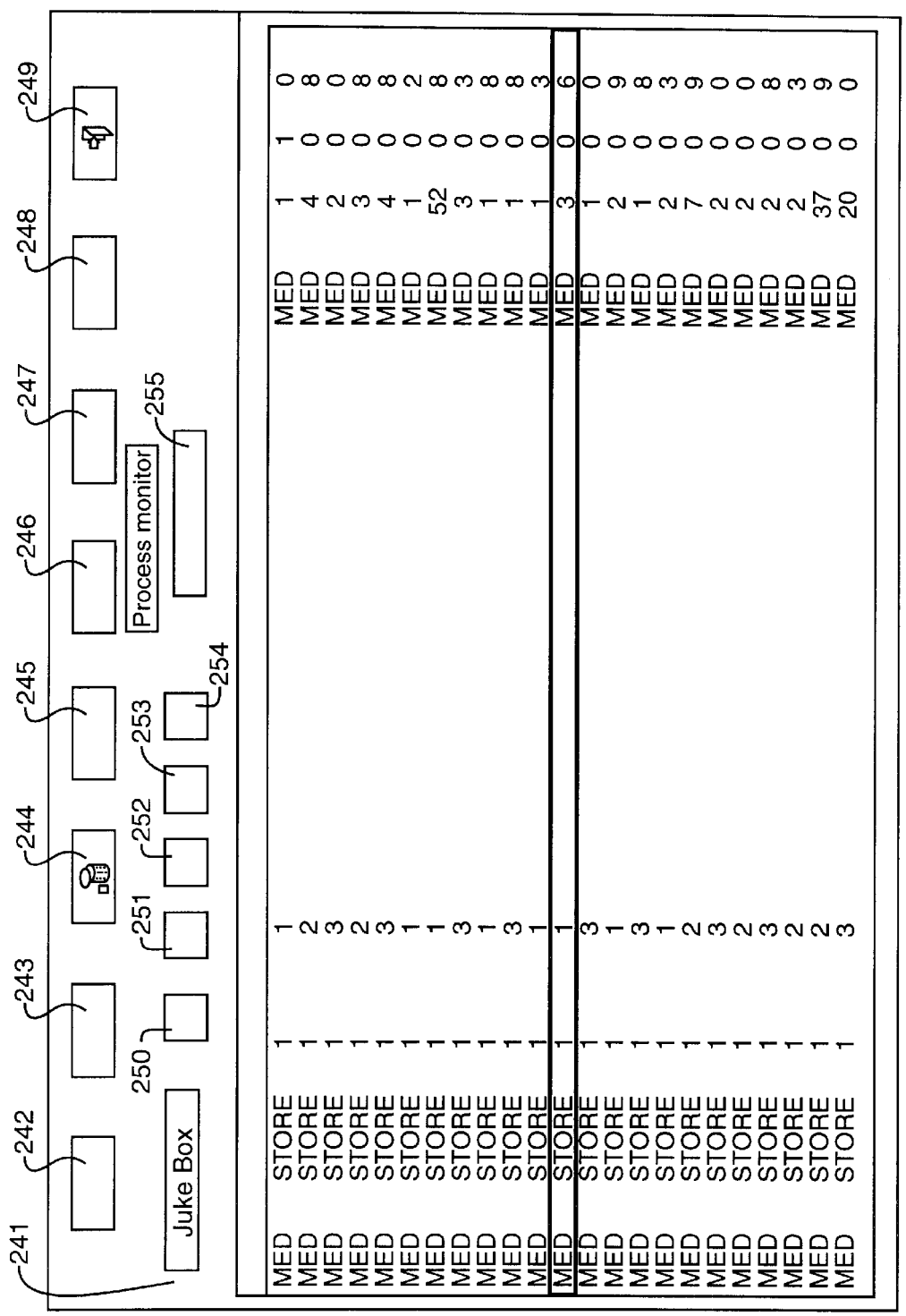
FIG. 21 shows a process monitor form.

FIG. 21 shows the preferred format of the process monitor form noted in sections 3.1 and 4.2 above. As shown in the figure, the process monitor form includes two rows of action buttons, which allow the user to control queue activity of stations in the PACS. The top row of action buttons allows a user to halt local queues, restart local queues, delete unwanted or stuck print jobs, increase or decrease the priority of selected print jobs, and retry printing of jobs that have failed or that are stuck in "printing in progress" status. The second row of action buttons provides different selection criteria which facilitate image viewing.

Depending upon how the PACS is configured, there may be six or more general queues that the user can check using the process monitor. To select a queue, the user need only click on tab 241. In the example shown in FIG. 21, the jukebox queue is checked. Table 7 below shows what other queues may be checked and from where.

TABLE 7

| | Process Monitor | |
|---|---|---|
| Queue | From Which PACS Stations May Monitor The Queue | What Monitoring Shows |
| Jukebox (Archive) | All | Status of store and retrieve jobs between the optical disk jukebox and station(s) cache memory. |
| Auto-Pilot | All | Status of the process that automatically manages the migration of studies from cache memory to optical disk. |
| Import Gateway | Network Gateway | Status of studies that are being transmitted to the PACS from DICOM modalities and APIP sources. |
| OCR | Network Gateway | Status of APIP (direct video capture) jobs that are being processed for optical character recognition. |
| Retrieve | All | Status of retrieved jobs (i.e., incoming studies). |
| Transmit | All | Status of out-going (i.e., transmitted) jobs. |

With respect to the top row of action buttons shown in FIG. 21, button 242 halts a queue; button 243 restarts a halted queue; button 244 removes highlighted jobs from the queue (so long as printing is not in progress); button 245 increases the priority of a job in the queue; button 246 decreases the priority of a job in the queue; button 247 manually forces a job from a retry state into a new state; button 248 displays the volume ID of an optical disk that is not present in the jukebox; and button 249 closes the process monitor form. With respect to the bottom row of action buttons shown in FIG. 21, button 250 indicates a queue's status, e.g., whether it is running, halted, or halting; button 251 selects all items on a queue; button 252 de-selects items in the queue; button 253 selects jobs that are not in progress, but that have some destination (e.g., to a reviewing station, RP5, or the like); button 254 select jobs that are not in progress, but that have the same identifier (e.g., accession number); and text entry window 255 allows the user to enter text, including the identifier or destination mentioned above.

As shown in FIG. 21, each of the jobs in a queue has a status associated therewith. Progress means that a job is being processed and, therefore, cannot be deleted; New means that the job is new to the queue and is waiting behind others to be processed; Retry means that the job has failed at its first attempt, e.g., at printing; Error means that the job has attempted several retries to no avail and, therefore, user intervention is required; Suspended means that the job is suspended in an import gateway queue of the DICOM association while a corresponding modality remains open, and that no data is flowing to the PACS; Done means that the job has been completed; and Failed means that, after a maximum number of retries, the job has failed.

4.3 Virtual Screen Section

Figure 22:
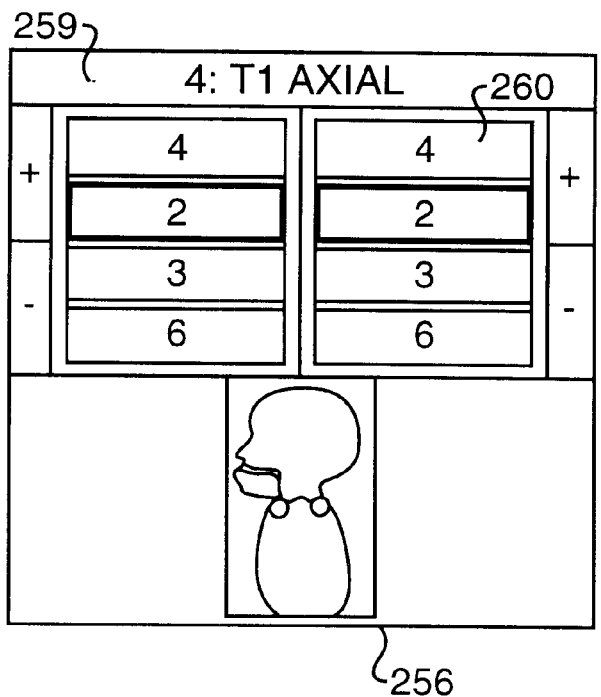
FIG. 22 shows the virtual screen section of the toolbar.

Virtual screen section 204 of toolbar 200 is a simplified map of how each of the video screens is being used to display a series of images. FIG. 22 shows an example of the use of virtual screen section 204. In that example, four images span across both screens, while the remaining images are represented by thumbnail images 256. In this regard, the two large squares 259 and 260 at the top of the virtual screen are called screen models. If a study has multiple images, then there will be additional icons displayed, called cells, as shown in the figure. The virtual screen section and the format selection section may be used together to create image layouts on a reviewing station's display screen.

Figure 23:
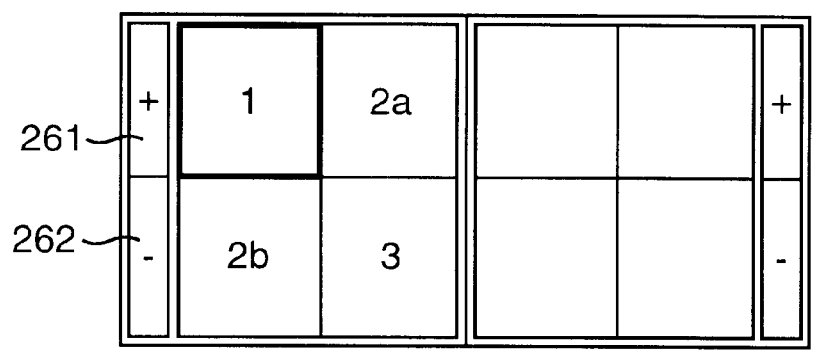
FIG. 23 shows virtual screens in the virtual screen section.

More specifically, FIG. 23 shows how virtual screen section 204 is used to set the format of the display. In this regard, the display format shown is "four-on-one stack mode", and the first series of images "1" is highlighted. Clicking on any of the cells together toggles their selection status. Clicking "+" button 261 selects all series that are displayed in the virtual screen; and clicking "−" button 262 de-selects all selected series displayed in the virtual screen. Series locations can be exchanged merely by selecting a series and dragging and dropping that series to a new location. The invention also provides an "MR cursor mode" (described below), whereby when an MR study is displayed, and the user may navigate through images in studies displayed on the virtual screen by using a single image as a reference.

4.4 Image Manipulation Section

Image manipulation section 203 of toolbar 200 includes folder tabs that allow users to select among various operating modes. The number and types of these user tabs is profile-dependent, meaning that they may vary based on inputs to the user's profile. In preferred embodiments of the invention, the tabs include window/level tab 263, image processing and rotation tab 264, print tab 265, CT scout tab 267, cine tab 269, and markup tab 270. Selecting each of these tabs causes action buttons to be displayed for each operating mode.

Starting with window and level tab 263, after that tab is selected, several action buttons are displayed, together with a greyscale bar with numeric window and level readouts. This configuration is shown in FIG. 17. In the present invention, several different functions may be invoked via window and level tab 263. More specifically, clicking on button 280 displays the numeric window level values shown in the figure. Clicking on button 272 magnifies displayed image by a predetermined factor which is based on the number and type of clicks thereon. Clicking on button 273 brings the system into MR cursor mode. In this regard, MR cursor mode permits the user to navigate through MR images according to each individual image slice or to view all slices at once. In preferred embodiments of the invention, there are three display formats. These include four-on-one stack mode, whereby there are four slices per screen; nine-on-one stack mode, whereby there are nine slices per screen; and traditional sixteen-on-one strip mode, whereby there are sixteen strips per screen.

Button 274 allows the user to collimate an image, i.e., to isolate a portion of the image and then black-out the remaining area. This tool is especially powerful when used in combination with the magnification feature described above. Specifically, to collimate an image, the user clicks on the collimate button, and then drags a mouse outline around an area of the image to be collimated. Thereafter, the invention retrieves and displays only the image data for that image from its local cache, leaving the remainder of the screen black. Button 275 resets window level settings (including the information displayed in window 276) to what they were at the time of a last save; button 277 sets the window level settings back to the last window and level that were adjusted; button 278 inverts black and white levels of an image; button 232 saves the window settings; and button 279 allows the user to alter pre-set window level settings by displaying a form (not shown) that can be edited by the user to change, e.g., the study being reviewed, imaging modality, etc.

Figure 24:
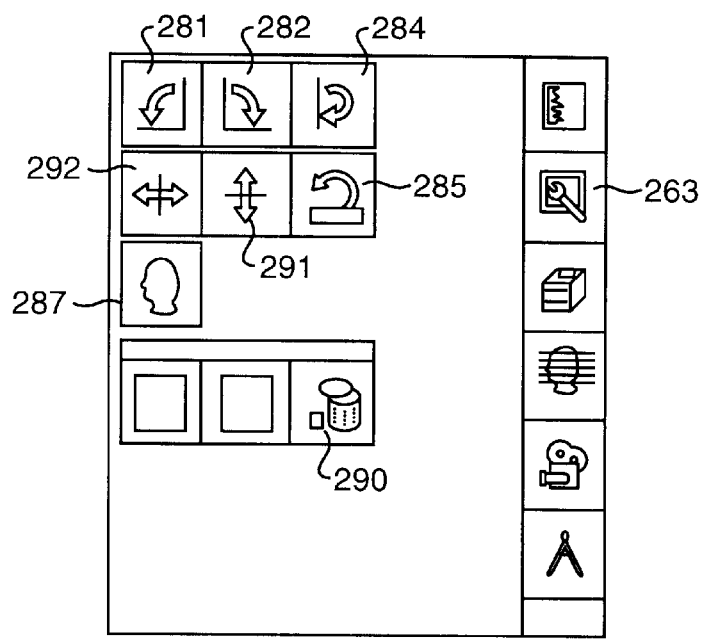
FIG. 24 shows tools displayed by the image processing tab in the toolbar.

Image processing tab 264 displays a different set of action buttons in section 203 than window and level tab 263. These are shown in FIG. 24. The buttons shown in FIG. 24 allow the user to perform basic quality assurance functions like rotating or flipping images. For example, button 281 rotates selected images 90° to the left; button 282 rotates selected images 90° to the right; button 291 flips selected images vertically; button 292 flips selected images horizontally; button 284 rotates selected images by 180°; button 287 rotates selected images by a user-set angle; button 285 resets the image to its original orientation; and button 290 deletes images.

Depending upon the modality that captured the images being displayed, and upon the user's profile, the image processing tab may also contain action buttons for hiding and re-ordering images. Although not shown in the figure, preferred embodiments of the invention contain four such action buttons, which allow the user, among other things, to hide images (meaning that the images are no longer displayed but remain in the study), to restore hidden images, to swap images (i.e., to switch positions of two images), and to insert images.

Figure 25:
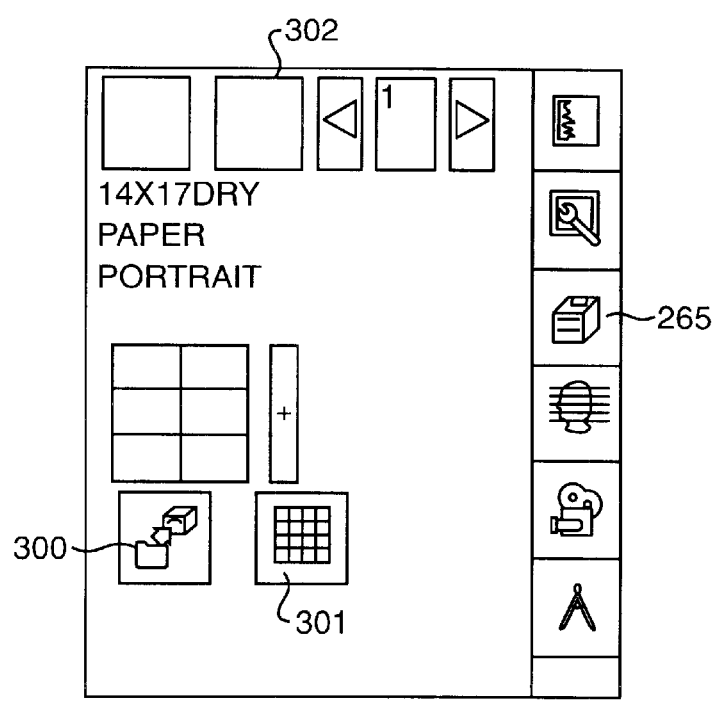
FIG. 25 shows tools displayed by the print tab in the toolbar.

Print tab 265 displays the set of buttons shown in FIG. 25 in section 203. These buttons allow a user to print an entire study, a selected series of images in a study, or a single image. Specifically, button 300 allows the user to print an entire study; and button 301 allows the user to print selected series of images in the virtual panel (which displays thumbnail versions of the images to be printed). Button 302 starts printing once image(s) have been selected from the virtual panel.

Figure 26:
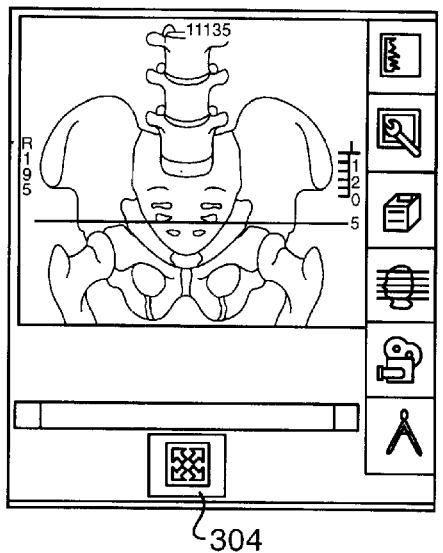
FIG. 26 shows a CT mode display.
Figure 27:
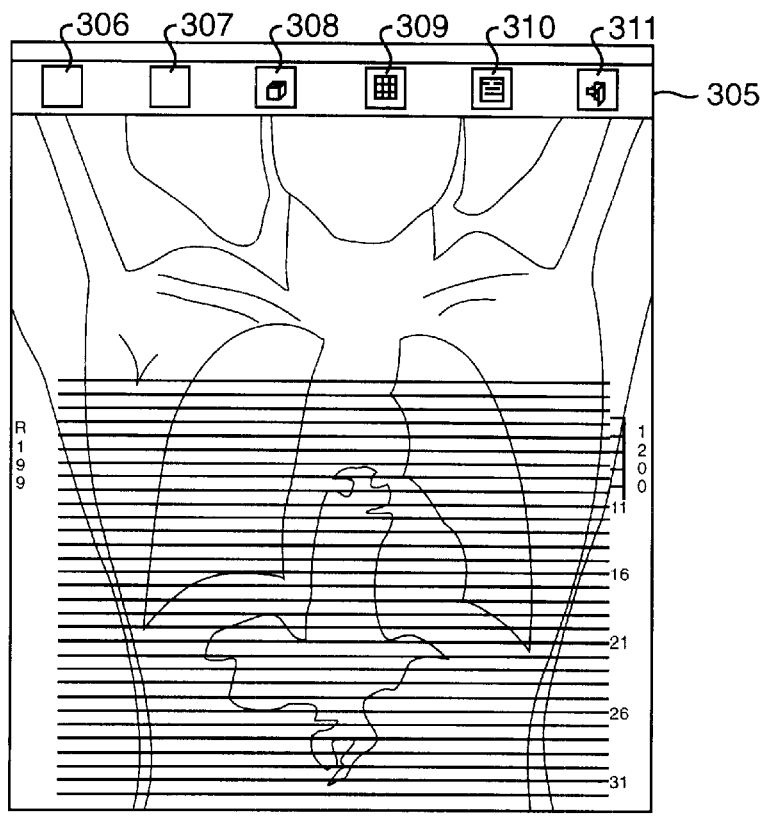
FIG. 27 shows an expanded CT mode display.

CT scout tab 267 is used when CT images are displayed by the PACS. In particular, FIG. 26 shows a CT image displayed on a reviewing station's display screen, together with the tabs noted above. As shown in FIG. 26, when a CT image is displayed, and CT scout tab 267 is activated, button 304 is also displayed. This button allows the user to expand the image to full-size merely by pointing and clicking. Once the image is expanded, as shown in FIG. 27, buttons 305 are also displayed. In this regard, button 306 adjusts the window level settings for the displayed image; button 307 displays all slice lines for the CT image; button 308 prints the image to a default printer (set, e.g, in the user profile); button 309 checks the summary, if any, for the displayed image; button 310 magnifies selected portions of the image; and button 311 closes the "expanded" window.

Figure 28:
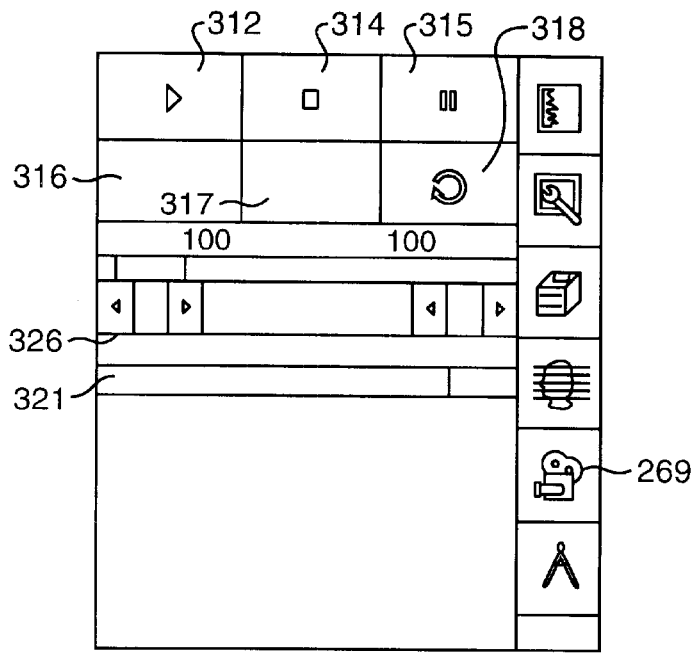
FIG. 28 shows tools displayed by the cine tab in the toolbar.

Cine tab 269 displays the action buttons, shown in FIG. 28, that allow the user to dynamically display some, or all, of the images in a series (e.g, to scroll automatically through the images on-screen). Button 312 starts' and stops "cine" mode; button 314 stops "cine" action and resets the display to the first image; button 315 pauses the "cine" action; button 316 moves back through displayed images, one image at a time; button 317 moves forward through the images, one image at a time; and button 318 toggles between "loop" mode, wherein images are displayed first-to-last, then repeated first-to-last (loop mode shown), and "rock" mode, wherein images are displayed first-to-last, and then repeated in descending order last-to-first. Slide bar 320 shown in FIG.

28 determines the ranges of images that are included in the cine loop and rock modes, whereas slider bar 321 determines the speed at which those images are displayed. In this regard, the invention allows the user to adjust the speed while the cine mode is running.

Figure 29:
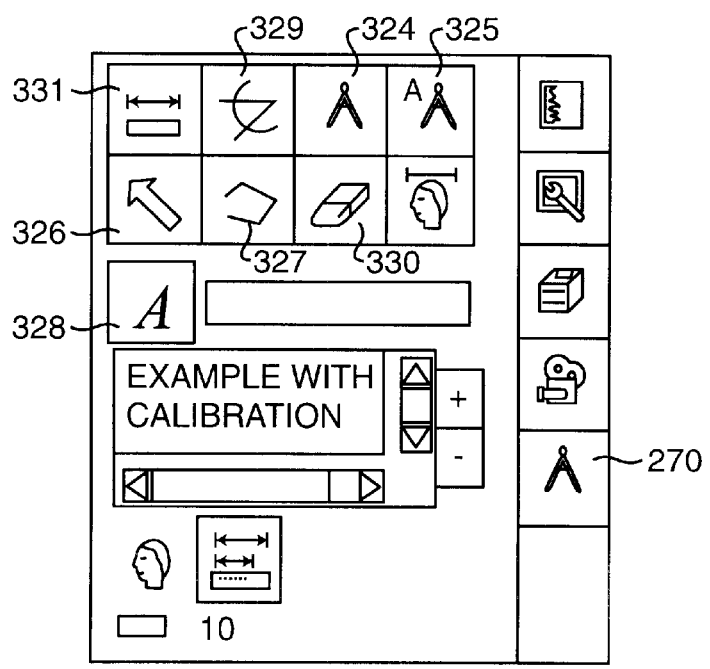
FIG. 29 shows tools displayed by the markup tab in the toolbar.

Markup tab 270 displays the action buttons shown in FIG. 29 in section 203. These action buttons allow the user to make straight line, angular, and optical density measurements of displayed images. They also display an annotation form whereby the user can create image overlays. More specifically, as shown in the figure, action buttons 324 and 325 allow the user to create elliptical regions of interest (i.e., regions which are to be edited) with or without text; button 326 allows the user to cut and paste arrows onto images; button 327 allows the user to select a region of interest; and button 328 allows a user to enter information relating to an image on an adjacent line. Button 329 allows the user to combine linear segments on an image and to measure an angle therebetween; button 330 allows the user to delete selected marks on an image; and button 331 allows the user to measure the distance (in pixels) between two selected endpoints within an image. Where there is no measurement data in the DICOM header for the image, the button may be calibrated to convert pixel distances into absolute measurement units, such as inches or centimeters.

5.0 User Profile

As noted above, the invention enables a PACS user to generate customized PACS displays. In brief, the invention is executable on a PACS station, and invokes display of at least one form (e.g., a user profile form or an access control form) having settable options for altering the PACS display, stores user inputs to the form(s) which correspond to the settable options, and generates the user-customized PACS display based, at least in part, on the user inputs to the form. In preferred embodiments of the invention, each user's profile is also provided to the database server, where it is stored, so that displays generated therefrom will appear at each login.

In more detail, clicking on the users button (see section 3.1 above) in the main study list opens up a set of folder tabs that allows the user to create accounts with associated profiles, manage application level security, and configure printing. These folder tabs include a user profile tab for assigning sort and selection criteria, display features, action buttons, film formats and other custom setting for each user; an access control tab for assigning site allowable features and privilege accessible features for each user; a user accounts tab for creating login names and assigning passwords and privilege levels; a printers tab for performing all DICOM print configuring, including modality-specific defaults, presets, and station-specific layouts; and a close tab for returning to the main study list.

Figure 30:
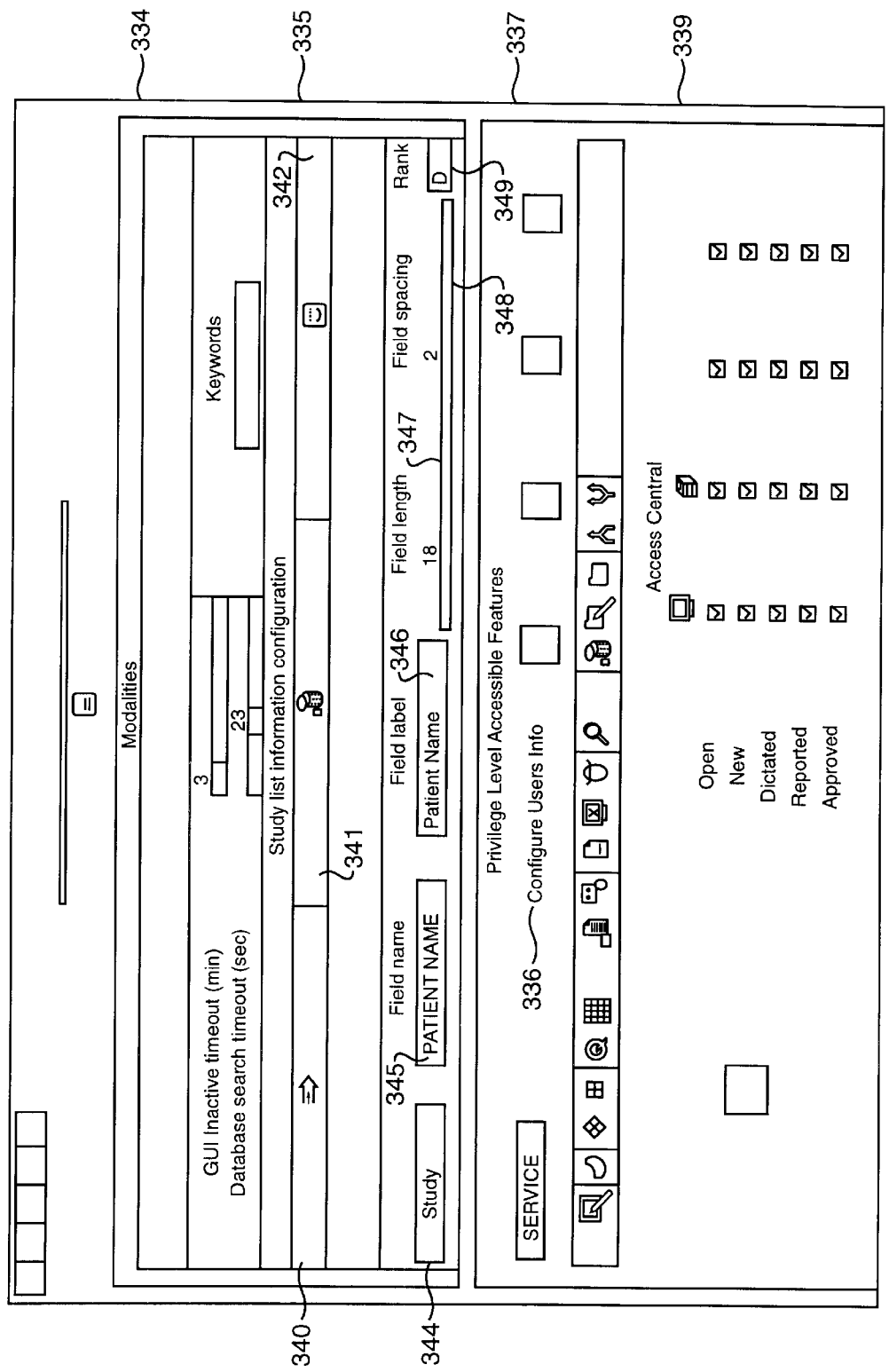
FIG. 30 shows an access control form.

Clicking on the access control tab displays the access control form shown in FIG. 30. This access control form is divided into five sections that allow the PACS administrator to assign global features and permission for all user login levels. As shown in the figure, these five sections include modalities section 334, study list information configuration section 335, configure user tabs section 336, privilege level accessible features section 337, and access control section 338.

Modalities section 334 is comprised of modality choices which, when selected, may be displayed in the modality sorting button of the main study window. This section also creates modalities selections in the printer configuration tab, which selections can be used to indicate the source of images being printed. Among the modalities which may be included in the modalities section are AS (angioscopy), BI (biomagnetic imaging), CD color flow doppler), CF (cinefluorography), CP (culdoscopy), CR (computed radiography), CS (cystoscopy), CT (computed tomography), DD (duplex doppler), DF (digital fluoroscopy), DG (diaphanography), DM (digital microscopy), DR (digital radiography), DS (digital subtraction angiography), EC (echocardiography), ES (endoscopy), FD (fluorescein angiography), FS (fundoscopy), LP (laparoscopy), LS (laser surface scan), MA (magnetic resonance angiography), MR (magnetic resonance), MS (magnetic resonance spectroscopy), MX (mixed modality—e.g., CR and DF in one study), NM (nuclear medicine), TO (other), PT (positron emission tomography), RG (radiographic imaging), RF (radio fluoroscopy), ST (single-photon emission CT), TG (thermography), US (ultrasound), VF (videofluorography), and XA (xeroradiography). This list is not meant to be exhaustive.

Study list information configuration section 335 configures column headings that appear in the main study list. In preferred embodiments of the invention, the user may set up three different layouts: patient, study, and patient & study. Button 340 adds a selected layout item to the main study list; button 341 deletes an item; and button 342 saves the changes. Study pull-down 344 selects study (shown), patient, or patient & study GUI layouts; field name pull-down 345 selects the field that the user is modifying, adding or deleting; field label text entry line 346 allows the user to type a new name for any selected field; field length slider 347 sets the maximum number of characters that a field can contain; field spacing slider 348 sets the number of blank spaces that separate adjacent fields; and rank pull-down 349 determines the relative position of a field. For example, a rank of zero (0) indicates the left-most position in the study list.

Configure users tabs section 336 determines which configuration tabs are available for each user. Privilege level accessible features 337 determines possible selections in the user profile form. Finally, access control section 338 indicates changes in study status as a study is read, dictated, reported and approved. That is, access control section 338 sets which study status that each login privilege may view, print, transmit or edit.

Figure 31:
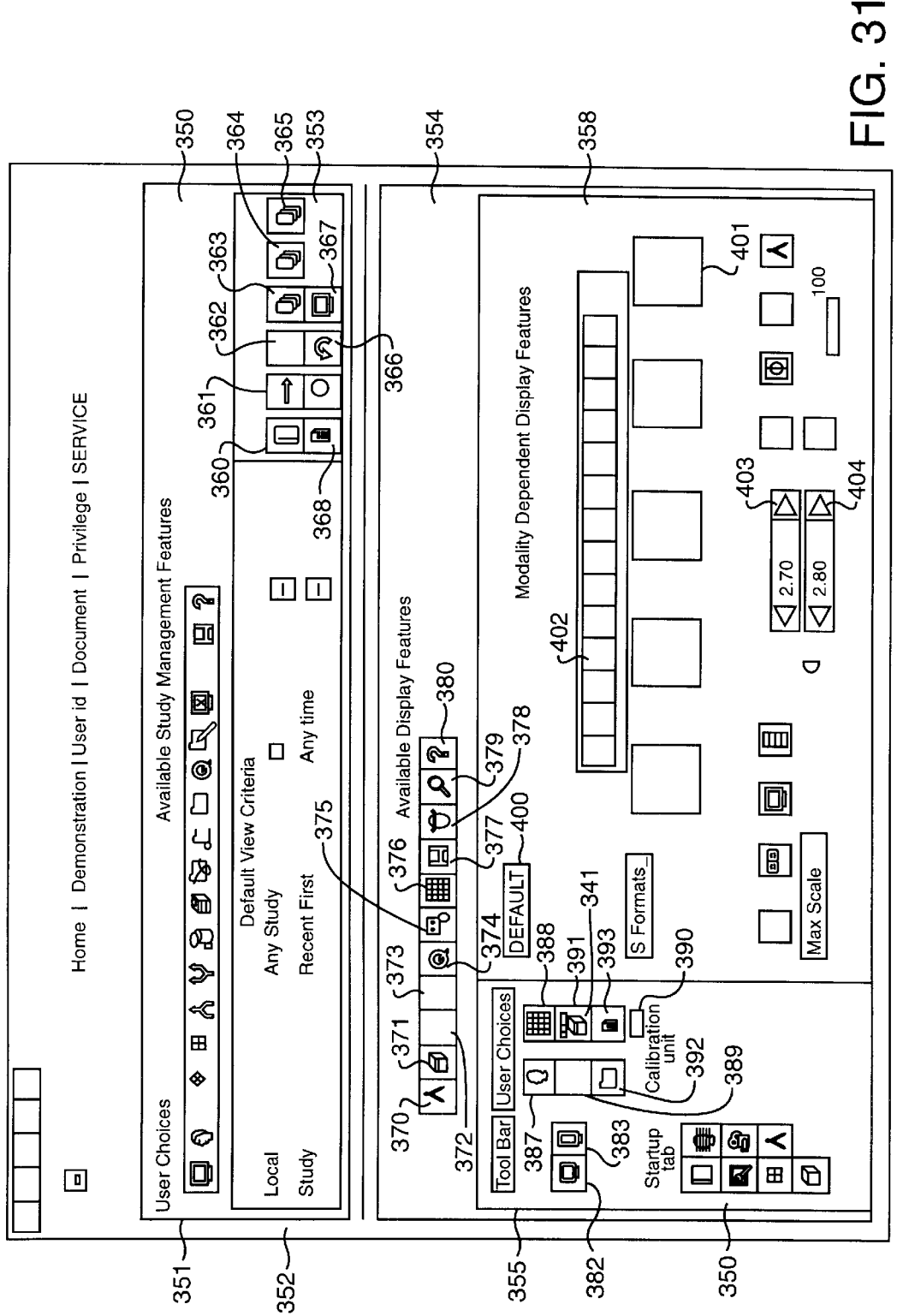
FIG. 31 shows a user profile form.

Clicking on the user profile tab displays the user profile form shown in FIG. 31. As shown, the user profile form is divided into several sections, whereby a user can customized the main study window and/or display toolbar. These sections include available study management features section 350 for selecting action buttons to appear in the main study window by clicking thereon; user choices section 351 for setting a sign-in mode and encoding patient names; default view criteria section 352 for sorting and selecting criteria in the main study window; worklist criteria section 353 for selecting features of the worklist; available display features section 354 for selecting action buttons and tabs in the display toolbar; tool bar section 355 for selecting a location of the toolbar on screen; startup tab section 356 for setting startup tabs in the toolbar; user choices section 357 for setting miscellaneous display defaults and measurement units, which includes displaying a patient's information form and prior RIS reports as defaults; and modality setup section 358 for selecting modalities for which formats and features are to be set.

With respect to study management features section, the action buttons which may be selected for display via that section are shown below in Table 8, together with the stations on which the selected buttons may appear.

TABLE 8

Selectable Action Buttons

| Button | Station |
|---|---|
| 1. Retrieve | RS |
| 2. Transmit | Any |
| 3. Merge | Gateway, AS |
| 4. Split Study | Gateway, AS |
| 5. Delete | RS |
| 6. Print | Any |
| 7. Protect | Any |
| 8. Report | Any |
| 9. Display Study Info | All |
| 10. Process Monitor | Any |
| 11. Copy to Jukebox | AS |
| 12. Delete from Jukebox | AS |
| 13. Copy to Cache | AS |
| 14. Archive Admin. | AS |
| 15. Backup Database | Server |
| 16. Fix Study | Any |
| 17. HIS Window | Any |
| 18. Configure/Service | Any |
| 19. Save | Any |
| 20. Help Tips | Any |

Default view criteria section 352 of the user profile form permits a user to select which of the buttons, i.e., "Local", "Study", "Any Study", "Any Modality", "Recent Last", and "Any Time", is to be displayed in the main study list. The functionality of these buttons is described above in section 3.1. Worklist criteria section 353 permits the user to generate worklists using only one mouse click by clicking on a displayed action button. To this end, worklist criteria section 353 includes worklist selection rules button 360, which creates the worklist select button (see section 3.1) in the main study list. Clicking on this button causes other buttons to appear, so long as they have been set in the user profile form. These buttons include send (display) button 361 which permits a user to view partially local studies that are in the process of being retrieved to the user's station; worklist cached button 362 which permits the user to select all cached studies in the PACS cluster that meet remaining criteria; relevant priors button 363 that allows the user to select relevant prior studies; priors match modality button 364 that allows the user to "fine-tune" selection of prior studies; priors match speciality button 365 that further "fine-tunes" selection of prior studies; select worklist specialty button 366 that permits the user to select studies based on body part; select acquisition station button 367 that allows users to select studies from a particular imaging modalities, and study status button 368 for selecting a default status.

Available display features section 354 is generally only used to configure PACS reviewing stations (including physician and clinical stations), since those are the stations which are primarily used for image display. As above, clicking on the buttons in the user profile causes those buttons to appear in the display toolbar. Here, these buttons include image mark-up button 370 which creates an annotation tab for annotating displayed images; print button 371 which creates a print tab (or, alternatively, a "Printer Not Found" message if no printers are available); transmit button 372 which creates a transmit button; report button 373 which creates a report button, whereby the user can query the RIS gateway for patient reports; process monitor button 374 which is used to check on the status of retrieved, transmitted, and printed jobs; dictate button 375, which toggles between various status relating to report dictation, as described above; summary button 376 which allows the user to create summary series; save button 377 which allows the user to save display settings, including mark-up, rotation, window level, and others; cursor mode button 378 which creates "cursor mode" (described above) for viewing MR studies; magnifier button 379; and help tips button 380.

Tool bar section 355 permits a user to select where, on a display screen, the toolbar is to be placed. Button 382 allows the user to select a landscape format for the toolbar; whereas button 383 allows the user to select a portrait format for the toolbar. Startup tab section 350 sets the default operating mode for displayed studies, e.g., transmit, print, cine, fix, edit, etc. Descriptions of the action buttons set forth in the startup tab section are provided above. Calibration unit 384 allows the user to select among centimeters, millimeters, or inches as the measurement units of a display markup tab.

User choices section 357 creates default settings that affect display and print behavior. In particular, button 387 enables/disables display of DICOM header information with an image; button 388 enables/disables display of a listing of summary series in the main study list; button 389 separates images so that color images are sent to a color printer and black-and-white images are sent to a black-and-white printer (of course, this will not work unless both types of printers are attached to the PACS); button 390 sets default print mode (i.e., color or black-and-white); button 391 causes the PACS to use the print criteria contained in a DICOM print service object that is associated with each study; button 392 automatically opens a patient information form upon display of a study; and button 393 automatically displays a patient's prior reports each time a new study is displayed. Other buttons may be included as well to place the user at the main study list following login (preferably used in reviewing stations); to launch display of selected images (e.g., images in a worklist) immediately following login; and to cause the patient's name to be encoded in the main study list. This last button assures the patient's privacy.

Modality setup section 358 creates custom display layouts and features based on imaging modality. In this regard, default pull-down 400, when activated, displays modalities available on the PACS. A different display may then be generated for each modality, by selecting one or more action buttons. In this regard, the action buttons include a button which selects an entire series or study for window level display and other operations; a button which selects a single image for window level display and other operations; a button which displays one study per monitor; a button which displays one study per two monitors; a button which displays one study per four monitors; a button which combines different series of studies; a button which splits series of studies; a button which displays a single series of studies on all available monitors; a button which displays an individual series on each monitor; a button which changes the order of displayed images; a button which inverts black and white levels of an image; a button which provides image rotation tools under an image processing tab in the toolbar; a button which allows the user to define elliptical regions of interest under an annotation tab in the toolbar; a button which sets the default cine mode to loop; a button which sets the default cine mode to rock; and a button which disables cine mode.

Also included in the modality setup section is a scaling factor button. This button determines how large a one-mode image will appear in a display. Larger scaling factors create larger one-mode images which preferably do not exceed the maximum display resolution. For example, setting a scaling factor of four (4) for MR images will create full-screen, one-mode images on a 1K reviewing station. This results when the typical 256×256 image matrix is scaled up to 1024×1024. The same image and scaling factor on a 2K reviewing station would have a height approximately one-half the screen height.

Format selection list 401 shows available image formats for the various imaging modalities. Examples of such formats are described in section 4.2 above. The preferred embodiment of the invention permits the user to select, for the toolbar, up to five different formats per modality from the choices provided in 402; although the invention is not limited to this. The five selected display formats are then displayed in format list 401 on the user profile form. Finally, the user profile form allows the user to select gamma and alpha correction factors for each imaging modality via entry lines 403 and 404, respectively.

6.0 Pipeline Retrieval

As noted above, pipeline retrieval of images is initiated using display button 125 in the main study list. Pipeline retrieval of images is implemented and controlled by PACS software modules running on each PACS station. In particular, it is effected by computer-executable code on a PACS station (e.g., a reviewing station), which selects caches of different components, retrieves image data for designated studies from the selected caches, forms each image from the retrieved image data, and displays each image once it is formed (i.e., as it arrives), without waiting for image data for any additional images in the designated studies to arrive at the station.

More specifically, in the preferred embodiment of the present invention, to effect pipeline retrieval of images, the user selects cached studies from, e.g., the main study list, and then hits display button 125 to display those images. In response, the images are retrieved from various caches throughout the PACS. For example, the images may be retrieved from the network gateway's cache, the archive station's cache, etc. Thereafter, as data for each image arrives at the display station, an image is formed and displayed in real-time, rather than waiting for image data for all the requested images to reach the station. By displaying images in this manner, the invention reduces the amount of time required to display images (since it reduces unnecessary waiting).

It is noted that although the preferred embodiment of the invention implements pipeline retrieval interactively, the invention is not limited to this. Rather, pipeline retrieval can also be implemented automatically as well. For example, code can be included in the station to seek out all studies in the list with a "cached" status designation, and then to select caches associated with those studies. Similarly, although the primary benefits of pipeline retrieval are realized on reviewing stations, this feature can be included on any PACS station in a cluster.

The present invention has been described with respect to a particular illustrative embodiment. It is to be understood that the invention is not limited to the above-described embodiment and modifications thereto, and that various changes and modifications may be made by those of ordinary skill in the art without departing from the spirit and scope of the appended claims.

What is claimed is:

1. A picture archiving and communication system ("PACS") which handles images received from one or more external sources, the system comprising:

a plurality of reviewing stations, each of the plurality of reviewing stations being designated to receive images based on predetermined routing rules;

a network gateway which includes a processor to execute stored process steps so as (i) to receive the images from an external source, (ii) to determine which, if any, of the reviewing stations that each image should be routed to based on the predetermined routing rules, (iii) to route images to appropriate reviewing stations, (iv) to determine if any received images include additional information that is inconsistent with corresponding information previously stored on the PACS and (v) to correct the additional information in any such received images prior to routing the images;

a display screen which displays images routed thereto by the network gateway and a user interface generated by the PACS;

a memory which stores computer-executable process steps; and a processor which executes the process steps so as (i) to display the user interface, the user interface providing access to one or more forms for entering information to set the routing rules, and (ii) to relay the information back to the network gateway.

2. A PACS according to claim 1, wherein the predetermined routing rules route the images based on at least one of a set destination, a radiology specialty, image status, a referring physician, patient location, time, image category, and imaging modality.

3. A PACS according to claim 1, wherein the predetermined routing rules are settable by a user of the PACS.

4. A PACS according to claim 1, wherein the network gateway updates any pre-existing routing rules with the information provided by the at east one reviewing station.

5. A PACS according to claim 1, wherein the routing performed by the network gateway comprises organ-based routing in which images are routed to reviewing stations based on bodily organs that the images depict.

6. A PACS according to claim 1, further comprising:

a plurality of other stations, the plurality of other stations being designated to receive images based on the predetermined routing rules;

wherein the processor in the network gateway executes stored process steps so as to route images to the other stations in accordance with the predetermined routing rules.

7. A picture archiving and communication system ("PACS") which pre-fetches images or summaries of images in response to a scheduled event, the system comprising:

at least one station capable of displaying the images; and a network gateway which communicates with the at least one station and a remote source, the network gateway including a processor which executes stored process steps (i) to receive information concerning the scheduled event from the remote source, (ii) to query the remote source for details on the scheduled event, (iii) to receive the details from the remote source, (iv) to retrieve images from a memory on the PACS based on the details and one or more predetermined pre-fetching rules, (v) to determine if any received images include additional information that is inconsistent with corresponding information previously stored on the PACS, and (vi) to correct the additional information in any such received images prior to routing the images.

8. A PACS according to claim 7, wherein the processor on the network gateway executes process steps so as to route the retrieved images to the at least one station.

9. A PACS according to claim 7, wherein the at least one station comprises a cache-less reviewing station; and wherein the processor on the network gateway executes process steps so as (i) to store the retrieved images in memory, and (ii) to wait for a request from the cacheless reviewing station before routing the retrieved images thereto.

10. A PACS according to claim 9, wherein the predetermined pre-fetching rules comprise one or more of the following:

a rule for retrieving images based on a radiology specialty relating to the images;

a rule for retrieving images based on an imaging modality used to capture the images;

a rule for retrieving images relating to a same radiology specialty as a newly-acquired image;

a rule for retrieving images captured by a same imaging modality as the newly-acquired image;

a rule for retrieving images captured after a certain date;

a rule for retrieving summaries of the images along with the images;

a rule for routing retrieved studies to destinations set by predetermined routing rules; and a rule indicating whether retrieved studies are to remain in a PACS station's cache.

11. A PACS according to claim 10, wherein the predetermined routing rules route the images based on at least one of a set destination, a radiology specialty, image status, a referring physician, patient location, time, image category, and imaging modality.

12. A PACS according to claim 7, wherein the predetermined pre-fetching rules may be set by a user of the PACS.

13. A PACS according to claim 12, wherein the at least one station comprises:

a display screen capable of displaying the retrieved images and of displaying a user interface generated by the PACS;

a memory which stores computer-executable process steps; and a processor which executes the process steps so as (i) to display the user interface, the user interface providing access to one or more forms for entering information to set the pre-fetching rules, and (ii) to relay the information back to the network gateway.

14. A workstation which retrieves images from one of a plurality of caches located in different components of a picture archiving and communication system ("PACS") cluster, the workstation comprising:

a display screen capable of displaying images;

one or more memories which store computer-executable process steps and a list of studies, each study comprising one or more images; and a processor which executes the process steps stored in the one or more memories so as to retrieve image data for designated studies in the study list and to form images on the display screen using the image data, the process steps comprising code (i) to select caches of different components, (ii) to retrieve image data for designated studies from caches of the selected components, (iii) to form each image in the studies from retrieved image data, and (iv) to display each image on the display screen once the image is formed, without waiting for any additional image data to arrive, wherein the PACS cluster includes a network gateway having a processor, wherein the processor in the network gateway further executes stored process steps so as (i) to determine if any received images include additional information that is inconsistent with corresponding information previously stored on the PACS, and (ii) to correct the additional information in any such received images prior to routing the images.

15. A workstation according to claim 14, wherein the processor selects caches of different components in response to a PACS user input.

16. A workstation according to claim 15, wherein the processor executes process steps so as to display a user interface which includes a list of studies, at least one of which has a "cached" status designation associated therewith; and wherein the user input comprises selecting at least one of the studies in the list which has the "cached" status designation associated therewith.

17. A workstation in a picture archiving and communication system ("PACS") which generates a user-customized PACS display, the workstation comprising:

a memory which stores computer-executable process steps; and a processor which executes the process steps stored in the memory so as (i) to invoke display of at least one form, the form including settable options for altering the PACS display, (ii) to store user inputs to the form which correspond to the settable options, and (iii) to generate the user-customized PACS display based, at least in part, on the user inputs to the form, wherein the PACS includes a network gateway having a processor, wherein the processor in the network gateway further executes stored process steps so as (i) to determine if any received images include additional information that is inconsistent with corresponding information previously stored on the PACS, and (ii) to correct the additional information in any such received images prior to routing the images.

18. A workstation according to claim 17, wherein the PACS display comprises a list of studies, each study comprising one or more images, and a plurality of action buttons; and wherein the form includes options to select the plurality of action buttons.

19. A workstation according to claim 18, wherein the plurality of action buttons comprise two or more of the following: an image mark-up button for creating an annotation tab for annotating displayed images, a print button for creating a print tab, a transmit button for transmitting displayed images; a report button for querying a remote source for patient reports, a process monitor button for checking a status of retrieved, transmitted, and printed images, a dictate button for use in dictating reports on displayed images, a summary button for creating a summary for displayed images, a save button for saving display settings, a cursor mode button for viewing MR studies, a magnifier button, and a help tips button.

20. A workstation according to claim 18, wherein the processor invokes a second form also including settable options for altering the PACS display, the second form including options to configure the list of studies.

21. A workstation according to claim 20, wherein the second form includes options to select modality information that may be displayed in connection with the list of studies.

22. A workstation according to claim 18, Wherein the plurality of action buttons comprise two or more of the following: a retrieve button for retrieving studies, a transmit button for transmitting studies, a merge button for merging studies, a split study button for splitting studies, a delete button for deleting studies, a print button for printing studies, a protect button for protecting studies, a report button for generating study reports, a display study info button for displaying information relating to studies, a process monitor button for monitoring study status, a copy to jukebox button for copying studies to a memory archive, a delete from jukebox button for deleting studies from the memory archive, a copy to cache button for copying studies to a cache on the PACS, an archive administration button for managing the memory archive, a backup database button for removing local references to archived studies, a fix study button for correcting information in received studies, an HIS window button for opening a telnet session between the PACS and a networked information system, a configure button for configuring the PACS, a save button for saving inputs to the form, and a help tips button for providing help tips regarding the form.

23. A workstation according to claim 17, further comprising a display screen which displays one or more images and the PACS display;

wherein the PACS display comprises a toolbar that is displayed concurrently with the images, the toolbar including a plurality of action buttons which affect display of the images.

24. A workstation according to claim 23, wherein the form includes options affecting where on the display screen the tool bar is displayed and a format of the toolbar.

25. A workstation according to claim 23, wherein the form includes options to select the plurality of action buttons.

26. A workstation according to claim 17, further comprising a display screen which displays images and the user-customized PACS display;

wherein the user-customized PACS display includes action buttons for manipulating displayed images.

27. A workstation according to claim 26, wherein the action buttons for manipulating displayed images include at least one of the following: an action button to collimate displayed images, an action button to affect the orientation of displayed images, an action button for re-ordering displayed images, action buttons for dynamically displaying images, action buttons particularly for use with CT images, and action buttons for adding information to displayed images.

28. A picture archiving and communication system ("PACS") having plural core components arranged in a cluster, the plural core components of the PACS comprising:

an archive station which includes a long-term memory for storing image data;

a reviewing station which includes a display for displaying images based on received image data;

a network gateway which interfaces to a non-core component so as to receive image data therefrom, and which routes the image data to at least one of the archive station and the reviewing station based on a set of rules in the network gateway, the network gateway having a processor, wherein the processor in the network gateway further executes stored process steps so as (i) to determine if any received images include additional information that is inconsistent with corresponding information previously stored on the PACS, and (ii) to correct the additional information in any such received images prior to routing the images; and a database server which manages access to the image data, and which stores information relating to the image data.

29. A method of routing images in a picture archiving and communication system ("PACS"), the PACS including (i) a plurality of reviewing stations each being designated to receive images based on predetermined routing rules, and (ii) a network gateway which receives images from one or more external sources, the method comprising the steps of:

receiving images from the one or more external sources at the network gateway;

determining if any received images include additional information that is inconsistent with corresponding information previously stored on the PACS;

correcting the additional information in any such received images prior to routing the images in the routing step;

determining, in the network gateway, which, if any, of the reviewing stations that each image should be routed to, based upon the predetermined routing rules; and routing the images to appropriate reviewing stations.

30. A method according to claim 29, wherein the predetermined routing rules route the images based on at least one of a set destination, a radiology specialty, image status, a referring physician, patient location, time, image category, and imaging modality.

31. A method according to claim 29, wherein the predetermined routing rules are settable by a user of the PACS.

32. A method according to claim 31, further comprising the step of setting the predetermined routing rules by (i) displaying a user interface on a display screen of a reviewing station, the user interface providing access to one or more forms for entering information to set the routing rules, (ii) entering information on the one or more forms to set the routing rules, and (iii) relaying the information back to the network gateway.

33. A method according to claim 32, wherein, in a case that there are pre-existing routing rules on the network gateway, the relaying step causes the pre-existing routing rules to be updated based on the information input via the one or more forms.

34. A method according to claim 29, wherein the routing step comprises organ-based routing in which images are routed to reviewing stations based on bodily organs that the images depict.

35. A method according to claim 29, wherein the PACS includes a plurality of other stations, the plurality of other stations being designated to receive images based on the predetermined routing rules; and wherein the method further comprises the step of routing images to the other stations in accordance with the predetermined routing rules.

36. A method according to claim 29, wherein the PACS comprises at least one peripheral connected to the network gateway, the at least one peripheral being designated to receive images based on the predetermined routing rules;

wherein the method further comprises the step of routing images to the at least one peripheral in accordance with the predetermined routing rules.

37. A method according to claim 36, wherein the at least one peripheral comprises one or more of the following:

a Web server which sends images received from the network gateway to a remote location on the Internet; and a printer which prints images received from the network gateway.

38. A method, for use in a picture archiving and communication system ("PACS"), of pre-fetching images or summaries of images in response to a scheduled event, the PACS including (i) at least one station that is capable of displaying the pre-fetched images, and (ii) a network gateway which communicates with the at least one station and a remote source, the method comprising the steps of:

receiving information concerning the scheduled event from the remote source;

querying the remote source for details on the scheduled event;

receiving the details from the remote source;

retrieving images or summaries of images from a memory on the PACS based on the details and one or more predetermined pre-fetching rules;

determining if any retrieved images include additional information that is inconsistent with corresponding information previously stored on the PACS; and correcting the additional information in any such retrieved images prior to routing the retrieved images to the at least one station.

39. A method according to claim 38, wherein the predetermined pre-fetching rules comprise one or more of the following:

a rule for retrieving images based on a radiology specialty relating to the images;

a rule for retrieving images based on an imaging modality used to capture the images;

a rule for retrieving images relating to a same radiology specialty as a newly-acquired image;

a rule for retrieving images captured by a same imaging modality as the newly-acquired image;

a rule for retrieving images captured after a certain date;

a rule for retrieving summaries of the images along with the images;

a rule for routing retrieved studies to destinations set by predetermined routing rules; and a rule indicating whether retrieved studies are to remain in a PACS station's cache.

40. A method according to claim 39, wherein the predetermined routing rules route the images based on at least one of a set destination, a radiology specialty, image status, a referring physician, patient location, time, image category, and imaging modality.

41. A method according to claim 40, further comprising the step of setting the predetermined pre-fetching rules in response to a PACS user's input.

42. A method according to claim 41, wherein the setting step comprises (i) displaying a user interface, the user interface providing access to one or more forms for entering information to set the pre-fetching rules, (ii) inputting information to set the pre-fetching rules into the one or more forms, and (iii) relaying the information back to the network gateway.

43. A method of retrieving images from one of a plurality of caches located in different components of a picture archiving and communication system ("PACS") cluster, the method comprising the steps of:

displaying a list of studies on a PACS station, each study comprising one or more images available via the PACS;

designating one or more of the studies;

retrieving image data for the designated studies by (i) selecting caches of different components, and (ii) retrieving image data for images in the studies from caches of the selected components;

determining if any of the retrieved image data includes additional information that is inconsistent with corresponding information previously stored on the PACS;

correcting the additional information in any such retrieved image data; and forming images on the PACS station based on the retrieved image data by (i) forming each image in the designated studies from the retrieved image data, and (ii) displaying each image on the PACS station once the image is formed, without waiting for any additional image data to arrive.

44. A method according to claim 43, wherein the retrieving step selects caches of different components in response to a PACS user input.

45. A method according to claim 44, wherein the retrieving step comprises (i) displaying a user interface which includes a list of studies, at least one of which has a "cached" status designation associated therewith, and (ii) selecting at least one of the studies in the list which has the "cached" status designation associated therewith.

46. A method according to claim 43, wherein the PACS comprises at least (i) a network gateway which receives images from at least one imaging modality, and which routes received images to various PACS stations, and (ii) an archive station which includes long-term memory for storing images received from the network gateway, the network gateway and the archive station each including a cache for short-term data storage; and wherein the retrieving step retrieves the image data for the designated images from a cache on the network gateway and a cache on the archive station.

47. A method of generating a user-customized display for a picture archiving and communication system ("PACS"), the PACS including a network gateway having a processor, which executes stored process steps so as (i) to determine if any received images include additional information that is inconsistent with corresponding information previously stored on the PACS, and (ii) to correct the additional information in any such received images and wherein the PACS further includes at least one station for displaying the user-customized display and a database server, the method comprising the steps of:

invoking display of at least one form on the station, the form including settable options for altering the PACS display;

storing, in a memory on the server, user inputs to the form which correspond to the settable options; and generating the user-customized PACS display based, at least in part, on the user inputs to the form.

48. A method according to claim 47, wherein the PACS display comprises a list of studies, each study comprising one or more images, and a plurality of action buttons; and wherein the form includes options to select the plurality of action buttons.

49. A method according to claim 48, wherein the plurality of action buttons comprise two or more of the following: an image mark-up button for creating an annotation tab for annotating displayed images, a print button for creating a print tab, a transmit button for transmitting displayed images; a report button for querying a remote source for patient reports, a process monitor button for checking a status of retrieved, transmitted, and printed images, a dictate button for use in dictating reports on displayed images, a summary button for creating a summary for displayed images, a save button for saving display settings, a cursor mode button for viewing MR studies, a magnifier button, and a help tips button.

50. A method according to claim 48, further comprising the step of invoking a second form also including settable options for altering the PACS display, the second form including options to configure the list of studies.

51. A method according to claim 50, wherein the second form includes options to select modality information that may be displayed in connection with the list of studies.

52. A method according to claim 48, wherein the plurality of action buttons comprise two or more of the following: a retrieve button for retrieving studies, a transmit button for transmitting studies, a merge button for merging studies, a split study button for splitting studies, a delete button for deleting studies, a print button for printing studies, a protect button for protecting studies, a report button for generating study reports, a display study info button for displaying information relating to studies, a process monitor button for monitoring study status, a copy to jukebox button for copying studies to a memory archive, a delete from jukebox button for deleting studies from the memory archive, a copy to cache button for copying studies to a cache on the PACS, an archive administration button for managing the memory archive, a backup database button for removing local references to archived studies, a fix study button for correcting information in received studies, an HIS window button for opening a telnet session between the PACS and a networked information system, a configure button for configuring the PACS, a save button for saving inputs to the form, and a help tips button for providing help tips regarding the form.

53. A method according to claim 47, further comprising a display screen which displays one or more images and the PACS display;

wherein the PACS display comprises a toolbar that is displayed concurrently with the images, the toolbar including a plurality of action buttons which affect display of the images.

54. A method according to claim 53, wherein the form includes options affecting where on the display screen the tool bar is displayed and a format of the toolbar.

55. A method according to claim 53, wherein the form includes options to select the plurality of action buttons.

56. A method according to claim 47, further comprising a display screen which displays images and the user-customized PACS display;

wherein the user-customized PACS display includes action buttons for manipulating displayed images.

57. A method according to claim 56, wherein the action buttons for manipulating displayed images include at least one of the following: an action button to collimate displayed images, an action button to affect the orientation of displayed images, an action button for re-ordering displayed images, action buttons for dynamically displaying images, action buttons particularly for use with CT images, and action buttons for adding information to displayed images.

* * * * *